US007799820B2

(12) United States Patent
Takahashi et al.

(10) Patent No.: US 7,799,820 B2
(45) Date of Patent: Sep. 21, 2010

(54) 2-HETEROCYCLE-SUBSTITUTED INDOLE DERIVATIVES FOR TREATING DIABETES AND ASSOCIATED CONDITIONS

(75) Inventors: Keiji Takahashi, Tsukuba (JP); Yoshio Ogino, Tsukuba (JP); Teruyuki Nishimura, Ushiku (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 69 days.

(21) Appl. No.: 11/992,555

(22) PCT Filed: Sep. 29, 2006

(86) PCT No.: PCT/JP2006/320010

§ 371 (c)(1),
(2), (4) Date: Mar. 25, 2008

(87) PCT Pub. No.: WO2007/037534

PCT Pub. Date: Apr. 5, 2007

(65) Prior Publication Data

US 2009/0118304 A1    May 7, 2009

(30) Foreign Application Priority Data

Sep. 30, 2005    (JP) .............................. 2005-288399

(51) Int. Cl.
*A61K 31/405* (2006.01)

(52) U.S. Cl. ............... 514/415; 544/405; 546/277.4; 548/128; 548/131; 548/143; 548/254; 548/375.1; 548/504; 548/518

(58) Field of Classification Search ............... 514/415; 544/405; 546/277.4; 548/128, 131, 143, 548/254, 375.1, 504, 518
See application file for complete search history.

(56) References Cited

U.S. PATENT DOCUMENTS

| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 6,040,449 | A | 3/2000 | Tsuchiya et al. |
| 6,239,152 | B1 | 5/2001 | Gordeev et al. |
| 7,253,286 | B2 | 8/2007 | Funahashi et al. |
| 2005/0272740 | A1 | 12/2005 | Dorsch et al. |

FOREIGN PATENT DOCUMENTS

| EP | 0 726 260 A1 | 8/1996 |
| EP | 1 600 442 | 2/2004 |
| EP | 1 598 349 | 11/2005 |
| EP | 1 935 890 | 9/2006 |
| JP | 2000 26430 | 1/2000 |
| WO | WO 02/32872 | 4/2002 |
| WO | WO 03/004488 | 1/2003 |
| WO | WO 2004/017963 | 3/2004 |
| WO | WO 2004/031179 | 4/2004 |
| WO | WO 2004/076420 | 9/2004 |
| WO | WO 2004/081001 | 9/2004 |
| WO | WO 2007/037534 | 4/2007 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Bauman et al., "Indole-2-carboxylic acids, a new class of hypoglycemic compounds", Biochemical Pharmacology, vol. 18, No. 5, pp. 1241-1243 (1969).
Grupe et al., "Transgenic Knockouts Reveal a Critical Requirement for Pancreatic B Cell Glucokinase in Maintaining Glucose Homeostasis", Cell, vol. 83, pp. 69-78 (1995 ).
Mitsunobu, O., "The Use of Diethyl Azodicarboxylate and Triphenylphosphine in Synthesis and Transformation of Natural Products", Synthesis, vol. 1, pp. 1-28 (1981).
Tani et al., "Studies on biologically Active Halogenated Compounds IV Synthesis and Antibaterial Activity of Fluorinated Quinoline Derivatives", Chemical and Pharmaceutical Bulletin, vol. 30, pp. 3530-3543, 1982.

(Continued)

*Primary Examiner*—James O Wilson
*Assistant Examiner*—Douglas M Willis
(74) *Attorney, Agent, or Firm*—Richard C. Billups; John C. Todaro

(57) ABSTRACT

Disclosed is a compound represented by the formula (I) below, which has a glucokinase-activating effect and is thus useful for treatment of diabetes or obesity, or a pharmaceutically acceptable salt thereof.

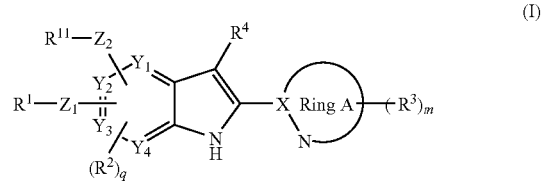

(I)

In the formula, $R^1$ represents an aryl or the like; $R^{11}$ represents an aryl or the like; $R^2$ represents a formyl or the like, $R^3$ represents a $C_{1-6}$ alkyl or the like; $R^3$ represents a hydrogen atom or the like; $Z_1$ represents —O— or the like; $Z_2$ represents —O— or the like; $Y_1$-$Y_4$ respectively represent a carbon atom or a nitrogen atom; ring A represents a heteroaryl group; X represents a carbon atom or the like; m represents an integer of 0-2; and q represents an integer of 0-2.

8 Claims, No Drawings

OTHER PUBLICATIONS

Tasneem et al., "Ammonium Nickel Sulphate Mediated Nitration of Aromatic Compounds with Nitric Acid", Synthetic Communications, vol. 31 (7), pp. 1123-1127, 2001.

Fonseca et al., "A short synthesis of phenanthrol[2,3-d]imidazoles from dehydroabietic acid. Application of the methodology as a convenient route to benzimidazoles" Tetrahedron, vol. 57, pp. 1793-1799, 2001.

Singh et al., "Synthetic Utility of Catalytic Fe(III)Fe(II) Redox Cycling Towards Fused Heterocycles: A Facile Access to Substituted Benzimidazole, Bis-benzimidazole and Imidazopyridine Derivatives" Synthesis, vol. 10, pp. 1380-1390, 2000.

Singh et al., "Reaction of 2-hydrazinobenzimidazole with B-diketones: A structural reinvestigation" Indian Journal of Chemistry, vol. 32, pp. 262-265, 1993.

Ferre et al., "Correction of diabetic alterations by glucokinase", Proc. Natl. Acad. Sci, vol. 93, pp. 7225-7230, 1996.

Glaser, B. et al., "Familial Hyperinsulinism Caused by an Activating Glucokinase Mutation" The new England Journal of Medicine, vol. 338, pp. 226-230, 1998.

Dolle, F. et al., "Synthesis and Nicotinic Acetylcholine Receptor in Vivo Binding Properties of 2-Fluoro-3-[2(S)-2-azetidinylmethoxy]pyridine: A New Position Emission Tomography Ligand for Nicotinic Receptors" J. Med. Chem, vol. 42, pp. 2251-2259, 1999.

Sitzmann, M. E. et al., "Fluronitroanilines Reaction Control via Hydrogen Bonding", J. Org. Chem, vol. 43, (6), pp. 1241-1243, 1978.

Vionnet, N. et al., "Nonsense mutation in the glucokinase gene causes early-onset non-insulin-dependent diabetes mellitus" Nature, vol. 356, pp. 721-722, 1992.

* cited by examiner

2-HETEROCYCLE-SUBSTITUTED INDOLE DERIVATIVES FOR TREATING DIABETES AND ASSOCIATED CONDITIONS

CROSS-REFERENCE TO RELATED APPLICATIONS

This application is a U.S. National Phase application under 35 U.S.C. §371 of PCT Application No. PCT/JP2006/320010, filed Sep. 29, 2006, which published as WO 2007/037534 on May 31, 2007, and claims priority under 35 U.S.C. §365(b) from Japanese patent application No. JP2005-288399, filed Sep. 30, 2005.

TECHNICAL FIELD

The present invention relates to a glucokinase activator comprising, as the active ingredient thereof, a 2-heteroaryl-substituted indole. Further, it relates to a novel 2-heteroaryl-substituted indole derivative.

BACKGROUND ART

Glucokinase (GK) (ATP: D-hexose 6-phosphotransferase, EC 2.7.1.1) is one (hexokinase IV) of four mammal hexokinases. Hexokinase is a first-stage enzyme in glycolysis and catalyzes a reaction from glucose to glucose hexaphosphate. In its expression, glucokinase is limited essentially in liver and pancreas beta cells, and it controls the rate-limiting step of glucose metabolism in these cells thereby playing an important role in systemic saccharometabolism. Glucokinase in liver and that in pancreas beta cells differ from each other in point of the N-terminal 15-amino acid sequence owing to the difference in splicing therebetween, but they are the same in point of the enzymatic property. The enzymatic activity of the other three hexokinases (I, II, III) than glucokinase is saturated at a glucose concentration of at most 1 mM, but Km of glucokinase to glucose is 8 mM and is near to a physiological blood-glucose level. Therefore, in accordance with the blood-glucose level change from a normal blood-glucose level (5 mM) to an increased blood-glucose level after meals (10 to 15 mM), intracellular glucose metabolism is accelerated via glucokinase.

Since ten years ago, a hypothesis that glucokinase may act as a glucose sensor in pancreas beta cells and liver has been proposed [for example, see Garfinkel D. et al's "Computer modeling identifies glucokinase as glucose sensor of pancreatic beta-cells", American Journal Physiology, Vol. 247 (3Pt2), 1984, pp. 527-536]. A result of recent glucokinase gene-manipulated mice has clarified that glucokinase actually plays an important role in systemic glucose homeostasis. Mice in which the glucokinase gene was disrupted die soon after their birth [for example, see Grupe A. et al's "Transgenic knockouts reveal a critical requirement for pancreatic beta cell glucokinase in maintaining glucose homeostasis", Cell, Vol. 83, 1995, pp. 69-78]; but on the other hand, normal or diabetic mice in which glucokinase was excessively expressed have a lowered blood-glucose level [for example, see Ferre T. et al's "Correction of diabetic alterations by glucokinase", Proceedings of the National Academy of Sciences of the U.S.A., Vo. 93, 1996, pp. 7225-7230]. With the increase in glucose concentration therein, the reaction of pancreas beta cells and that of liver cells are both toward the reduction in a blood-glucose level, though differing from each other. Pancreas beta cells come to secrete more insulin, and liver takes up sugar to store it as glycogen therein and simultaneously reduces sugar release.

To that effect, the change in the enzymatic activity of glucokinase plays an important role in mammal glucose homeostasis via liver and pancreas beta cells. In a juvenile diabetic case that is referred to as MODY2 (maturity-onset diabetes of the young), mutation of a glucokinase gene has been found, and the glucokinase activity reduction causes the blood-glucose level increase [for example, see Vionnet N. et al's "Nonsense mutation in the glucokinase gene causes early-onset non-insulin-dependent diabetes mellitus", Nature Genetics, Vol. 356, 1992, pp. 721-722]. On the other hand, a pedigree having mutation of increasing glucokinase activity has been found, and those of the family line show low blood-glucose level symptoms [for example, see Glaser B. et al's "Familial hyperinsulinism caused by an activating glucokinase mutation", New England Journal Medicine, Vol. 338, 1998, pp. 226-230].

From these, glucokinase acts as a glucose sensor and plays an important role in glucose homeostasis also in humans. On the other hand, blood-glucose level control by utilizing a glucokinase sensor system may be possible in many type-II diabetes patients. A glucokinase-activating substance may be expected to have an insulin secretion promoting effect in pancreas beta cells and have a sugar take-up accelerating and sugar release inhibiting activity in liver, and therefore it may be useful as a remedy for type-II diabetes patients.

Recently, it has become clarified that pancreas beta cell-type glucokinase is limitedly expressed locally in rat brains, especially in ventromedial hypothalamus (VMH) thereof. About 20% neurocytes in VMH are referred to as glucose-responsive neurons, and heretofore it has been considered they may play an important role in body weight control. When glucose is administered to a rat brain, then it reduces the amount of ingestion; but when glucose metabolism is retarded through intracerebral administration of glucosamine, a glucose analogue, then it causes hyperphagia. From an electrophysiological experiment, it is admitted that glucose-responsive neurons are activated in accordance with a physiological glucose concentration change (5 to 20 mM), but when glucose metabolisms is inhibited by glucosamine or the like, then their activity is retarded. In the glucose concentration-sensitive system in VMH, a glucose-mediated mechanism is anticipated like the insulin secretion in pancreas beta cells. Accordingly, there may be a possibility that a substance for glucokinase activation in VMH, in addition to liver and pancreas beta cells, may be effective not only for blood-glucose level correction but also for solution of obesity that is problematic in many type-II diabetes patients.

From the above description, a compound having a glucokinase activation effect is useful for remedies and/or preventives for diabetes, or for remedies and/or preventives for chronic complications of diabetes such as retinopathy, nephropathy, neurosis, ischemic cardiopathy, arteriosclerosis, and further for remedies and/or preventives for obesity.

As a compound structurally similar to the indole derivative (I) of the invention, for example, a compound represented by the following formula (A):

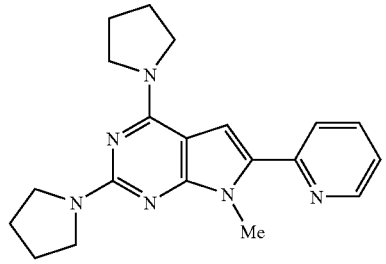

is disclosed (for example, see WO2002/032872).

The compound of the above formula (A) differs from the compound of the invention in that in the former, the amino group of the pyrrole ring of the pyrrolo[2,3-d]pyrimidine skeleton is protected with a methyl group, but in the latter, it is not protected. In addition, the two further differ in that, in the compound of the above formula (A), two aliphatic heterocyclic groups bond to the pyrrolo[2,3-d]pyrimidine skeleton, but the compound of the invention does not include those in which two aliphatic heterocyclic groups bond to the indole skeleton.

Moreover, the diseases to which the above formula (A) is directed are subarachnoid hemorrhage and ischemic stroke after it, etc.; and they differ from the diseases to which the compound of the invention is directed.

DISCLOSURE OF THE INVENTION

An object of the present invention is to provide a remedy and/or a preventive for diabetes, which bonds to glucokinase to increase the activity of glucokinase, and to provide an anti-obesity agent that activates glucokinase to stimulate a satiety center thereby exhibiting its effect.

The present inventors have assiduously studied in order to develop a novel drug for diabetes having, owing to the effect thereof differing from that of the above-mentioned already-existing drugs, a potency over that of the already-existing drugs for diabetes and having a novel potency, and as a result, have found that a compound represented by a formula (I) has a glucokinase-activating effect, and have completed the present invention. Specifically, the invention relates to the following:

(1) A compound represented by formula (I):

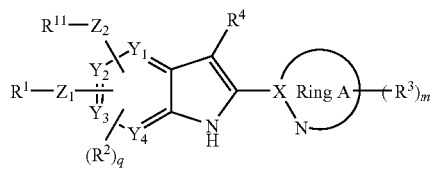

or a pharmaceutically acceptable salt thereof, wherein:

$R^1$ represents an aryl or a heteroaryl having from 1 to 3 hetero atoms selected from the group consisting of a nitrogen atom, a sulfur atom and an oxygen atom;

$R^{11}$ represents an aryl, or a 5- to 7-membered aliphatic hetero ring or a 5- or 6-membered heteroaryl having from 1 to 3 hetero atoms selected from the group consisting of a nitrogen atom, a sulfur atom and an oxygen atom;

said $R^1$ and $R^{11}$ may be mono to tri-substituted with the same or different $R^5$;

$R^2$ each independently represents formyl, —OH, —$C_{1-6}$ alkyl, —$CH_{3-a}F_a$, —$OCH_{3-a}F_a$, amino, cyano, halogen or —$(CH_2)_{1-4}$—OH;

$R^3$ each independently represent —$C_{1-6}$ alkyl, —$(CH_2)_{1-6}$—OH, —C(O)—$OC_{1-6}$ alkyl, —$(CH_2)_{1-6}$—$OC_{1-6}$ alkyl, —$(CH_2)_{1-6}$—$NH_2$, cyano, —C(O)—$C_{1-6}$ alkyl, halogen, —$C_{2-6}$ alkenyl, —$OC_{1-6}$ alkyl, —COOH or —OH;

$R^4$ represents a hydrogen atom or —$C_{1-6}$ alkyl;

$R^5$ each independently represents —$C_{1-6}$ alkyl optionally substituted with the same or different, from 1 to 3 hydroxy, halogen, —OC(O)—$C_{1-6}$ alkyl optionally substituted with from 1 to 3 halogens, or —$OC_{1-6}$ alkyl;

—$C_{3-7}$ cycloalkyl;

—$C_{2-6}$ alkenyl;

—C(O)—N($R^{51}$)$R^{52}$;

—S(O)$_2$—N($R^{51}$)$R^{52}$;

—O—$C_{1-6}$ alkyl optionally substituted with halogen or N($R^{51}$)$R^{52}$;

—S(O)$_{0-2}$—$C_{1-6}$ alkyl;

—C(O)—$C_{1-6}$ alkyl optionally substituted with halogen, amino, CN, hydroxy, —O—$C_{1-6}$ alkyl, —$CH_{3-a}F_a$, —OC(O)—$C_{1-6}$ alkyl, —N($C_{1-6}$ alkyl)C(O)O—$C_{1-6}$ alkyl, —NH—C(O)O—$C_{1-6}$ alkyl, phenyl, —N($R^{51}$)$R^{52}$, —NH—C(O)—$C_{1-6}$ alkyl, —N($C_{1-6}$ alkyl)-C(O)—$C_{1-6}$ alkyl or —NH—S(O)$_{0-2}$—$C_{1-6}$ alkyl;

—C(S)—$C_{3-7}$ cycloalkyl;

—C(S)—$C_{1-6}$ alkyl;

—C(O)—O—$C_{1-6}$ alkyl;

—$(CH_2)_{0-4}$—N($R^{53}$)—C(O)—$R^{54}$;

—N($R^{53}$)—C(O)—O—$R^{54}$;

—C(O)-aryl optionally substituted with halogen;

—C(O)-aromatic hetero ring;

—C(O)-aliphatic hetero ring;

a hetero ring optionally substituted with unsubstituted —$C_{1-6}$ alkyl or —$C_{1-6}$ alkyl substituted with halogen or —O—$C_{1-6}$ alkyl;

a phenyl optionally substituted with halogen, —$C_{1-6}$ alkyl or —O—$C_{1-6}$ alkyl;

a halogen, CN, formyl, COOH, amino, oxo, hydroxy, hydroxyamidino or nitro;

$R^{51}$ and $R^{52}$ each independently represent a hydrogen atom or —$C_{1-6}$ alkyl, or the nitrogen atom;

$R^{51}$ and $R^{52}$, taken together, form a 4- to 7-membered hetero ring;

$R^{53}$ represents a hydrogen atom or —$C_{1-6}$ alkyl;

$R^{54}$ represents —$C_{1-6}$ alkyl, or the alkyl of $R^{53}$ and $R^{54}$ and —N—C(O)—, taken together, form a 4- to 7-membered, nitrogen-containing aliphatic hetero ring, or the alkyl of $R^{53}$ and $R^{54}$ and —N—C(O)—O—, taken together, form a 4- to 7-membered, nitrogen-containing aliphatic hetero ring optionally substituted with oxo, or the aliphatic hetero ring may have 1 or 2 double bonds in the ring;

Y represents a carbon atom or a nitrogen atom;

$Z_1$ represents —O—, —S—, —S(O)— or —S(O)$_2$—;

$Z_2$ represents —O—, —S—, —S(O)—, —S(O)$_2$—, —$CH_2$— (the —$CH_2$— may be substituted with halogen, $C_{1-6}$ alkyl, hydroxy, cyano or —O—$C_{1-6}$ alkyl), or a single bond;

$Y_1$ to $Y_4$ are such that at least two of $Y_1$ to $Y_4$ are carbon atoms, and the remainder are a carbon atom or a nitrogen atom;

the ring A represents a heteroaryl group having, in the ring, from 1 to 4 hetero atoms selected from the group consisting of a nitrogen atom, a sulfur atom and an oxygen atom, and represented by a formula (II):

X represents a carbon atom or a nitrogen atom, m indicated an integer of from 0 to 2;

q indicates an integer of from 0 to 2;

(2) The compound according to the above (1), wherein the ring A is thiazolyl, imidazolyl, isothiazolyl, thiadiazolyl, oxadiazolyl, triazolyl, oxazolyl, isoxazolyl, pyrazinyl, pyridyl, pyridazinyl, pyrazolyl or pyrimidinyl optionally substituted with from 1 to 3 $R^5$'s; or a pharmaceutically acceptable salt thereof;

(3) The compound according to the above (1), wherein the formula (I) is a formula (I-1):

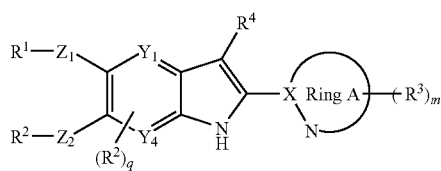

(I-1)

or a formula (I-2):

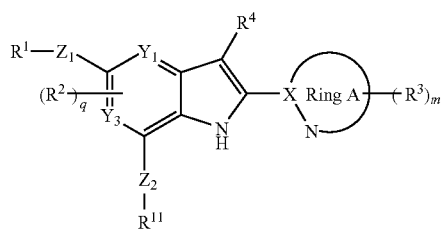

(I-2)

wherein the symbols are the same as above;

or a pharmaceutically acceptable salt thereof;

(4) The compound according to any one of the above (1) to (3), wherein $R^{11}$ is an aryl, or a pharmaceutically acceptable salt thereof;

(5) The compound according to any one of the above (1) to (3), wherein $R^{11}$ is a 5- to 7-membered aliphatic hetero ring having, in the ring, from 1 to 3 hetero atoms selected from the group consisting of a nitrogen atom, a sulfur atom and an oxygen atom, or a pharmaceutically acceptable salt thereof.

(6) The compound according to any one of the above (1) to (3), wherein $R^{11}$ is a 5- or 6-membered heteroaryl group having, in the ring, from 1 to 3 hetero atoms selected from the group consisting of a nitrogen atom, a sulfur atom and an oxygen atom, or a pharmaceutically acceptable salt thereof;

(7) The compound according to the above (1), wherein any one of $Y_1$ to $Y_4$ is a nitrogen atom, or a pharmaceutically acceptable salt thereof;

(8) The compound according to the above (1), wherein the compound of formula (I) is:

7-(2-fluorophenoxy)-5-(4-(methylsulfonyl)phenoxy)-2-pyridin-2-yl-1-indole, 7-(2-fluorophenoxy)-5-(4-(methylsulfonyl)phenoxy)-2-pyrazin-2-yl-1H-indole, 7-(2,6-difluorophenoxy)-5-(4-(methylsulfonyl)phenoxy)-2-pyrazin-2-yl-1H-indole, 7-(2,6-difluorophenoxy)-5-((6-(methylsulfonyl)pyridin-3-yl)oxy)-2-pyridin-2-yl-1H-indole, 7-(2,6-difluorophenoxy)-5-(4-(ethylsulfonyl)phenoxy)-2-pyrazin-2-yl-1H-indole, 7-(2,6-difluorophenoxy)-5-((6-(ethylsulfonyl)pyridin-3-yl)oxy)-2-pyridin-2-yl-1H-indole, 7-(2-cyanophenoxy)-5-((6-(ethylsulfonyl)pyridin-3-yl)oxy)-2-pyridin-2-yl-1H-indole, 2-((5-((6-(methylsulfonyl)pyridin-3-yl)oxy)-2-pyridin-2-yl-1H-indol-6-yl)oxy)-3-fluorobenzonitrile, 2-((5-((6-(ethylsulfonyl)pyridin-3-yl)oxy)-2-pyridin-2-yl-1H-indol-6-yl)oxy)-3-fluorobenzonitrile, 1-methyl-3-((5-(4-methylsulfonyl)phenoxy)-2-pyridin-2-yl-1H-indol-7-yl)oxy)pyridin-2(1H)-one, 1-methyl-3-((5-(4-ethylsulfonyl)phenoxy)-2-pyridin-2-yl-1H-indol-7-yl)oxy)pyridin-2(1H)-one, 5-((6-(ethylsulfonyl)pyridin-3-yl)oxy-7-(2-methoxyphenoxy)-2-pyridin-2-yl-1H-indole, 5-((6-(ethylsulfonyl)pyridin-3-yl)oxy-7-((2-methoxypyridin-3-yl)oxy)-2-pyridin-2-yl-1H-indole, 6-((2-(difluoromethoxy)pyridin-3-yl)oxy)-5-((6-(ethylsulfonyl)pyridin-3-yl)oxy)-2-pyridin-2-yl-1H-indole, 6-((2-(difluoromethoxy)pyridin-3-yl)oxy)-5-((6-(ethylsulfonyl)pyridin-3-yl)oxy-2-pyrazin-2-yl-1H-indole, 6-((2-(difluoromethoxy)pyridin-3-yl)oxy)-5-(4-(ethylsulfonyl)phenoxy)-2-pyridin-2-yl-1H-indole, 6-((2-(difluoromethoxy)pyridin-3-yl)oxy)-5-((6-(methylsulfonyl)pyridin-3-yl)oxy-2-pyridin-2-yl-1H-indole, 6-((2-chloropyridin-3-yl)oxy)-5-((6-(ethylsulfonyl)pyridin-3-yl)oxy-2-pyridin-2-yl-1H-indole, 3-((5-((6-(ethylsulfonyl)pyridin-3-yl)oxy)-2-pyridin-2-yl-1H-indol-6-yl)oxy)pyridin-2-carbonitrile, 6-(2,6-difluorophenoxy)-5-((6-(ethylsulfonyl)pyridin-3-yl)oxy)-2-pyrazin-2-yl-1H-indole, 6-(2,6-difluorophenoxy)-5-((6-(ethylsulfonyl)pyridin-3-yl)oxy)-2-pyridin-2-yl-1H-indole, 6-(2,6-difluorophenoxy)-5-((6-(ethylsulfonyl)pyridin-3-yl)oxy)-2-(1-methyl-1H-pyrazol-3-yl)-1H-indole, 6-(2,6-difluorophenoxy)-5-((6-(ethylsulfonyl)pyridin-3-yl)oxy)-2-(H-pyrazol-3-yl)-1H-indole, 6-(2,6-difluorophenoxy)-5-((6-(ethylsulfonyl)pyridin-3-yl)oxy)-2-(1,2,4-thiadiazol-5-yl)-1H-indole, 6-(2,6-difluorophenoxy)-5-((6-(ethylsulfonyl)pyridin-3-yl)oxy)-2-(1,3-thiadiazol-2-yl)-1H-indole, 2-((5-(4-(methylsulfonyl)phenoxy)-2-pyridin-2-yl-1H-indol-6-yl)oxy)benzamide, 4-((6-(2-aminocarbonyl)phenoxy)-2-pyridin-2-yl-1H-indol-5-yl)oxy)-N,N-dimethylbenzamide, 2-((5-((6-(ethylsulfonyl)pyridin-3-yl)oxy)-2-pyridin-2-yl-1H-indol-6-yl)oxy)benzonitrile, 2-((5-((6-(ethylsulfonyl)pyridin-3-yl)oxy)-2-pyrazin-2-yl-1H-indol-6-yl)oxy)benzonitrile, 5-((6-(ethylsulfonyl)pyridin-3-yl)oxy-6-((2-methoxypyridin-3-yl)oxy)-2-pyridin-2-yl-1H-indole, 5-((6-(ethylsulfonyl)pyridin-3-yl)oxy-6-(2-methoxyphenoxy)-2-pyridin-2-yl-1H-indole, 1-((5-((6-(methylsulfonyl)pyridin-3-yl)oxy)-2-pyridin-2-yl-1H-indol-6-yl)methyl)pyrrolidin-2-one, 1-((5-((6-(5-methyl-1,2,4-oxadiazol-3-yl)pyridin-3-yl)oxy)-2-pyridin-2-yl-1H-indol-6-yl)methyl)pyrrolidin-2-one, 1-((3-methyl-5-((6-(methylsulfonyl)pyridin-3-yl)oxy)-2-pyridin-2-yl-1H-indol-6-yl)methyl)pyrrolidin-2-one, 1-((5-((6-(methylsulfonyl)pyridin-3-yl)oxy)-2-pyrazin-2-yl-1H-indol-6-yl)methyl)pyrrolidin-2-one, 1-((5-((6-(ethylsulfonyl)pyridin-3-yl)oxy)-2-pyridin-2-yl-1H-indol-6-yl)methyl)pyrrolidin-2-one, 1-((5-(4-(ethylsulfonyl)phenoxy)-2-pyridin-2-yl-1H-indol-6-yl)methyl)pyrrolidin-2-one, 1-((5-(4-(5-methyl-1,2,4-oxadiazol-3-yl)phenoxy)-2-pyridin-2-yl-1H-indol-6-yl)methyl)pyrrolidin-2-one, 1-((5-((6-(methoxymethyl)pyridin-3-yl)oxy)-2-pyrazin-2-yl-1H-indol-6-yl)methyl)pyrrolidin-2-one, 1-((5-((6-(methoxymethyl)pyridin-3-yl)oxy)-2-pyridin-2-yl-1H-indol-6-yl)methyl)pyrrolidin-2-one, 5-(4-methylsulfonyl)phenoxy)-6-((1-methyl)-1H-tetrazol-5-yl)methyl)-2-pyridin-2-yl-1H-indole, 3-((5-((6-ethylsulfonyl)pyridin-3-yl)oxy)-2-pyridin-2-yl-1H-indol-6-yl)methyl)-1,3-oxazolidin-2-one, 3-((5-((6-ethylsulfonyl)pyridin-3-yl)oxy)-2-pyridin-2-yl-1H-indol-6-yl)methyl)-1,3-thiazolidin-2-one, 6-(1-acetylpyrrolidin-2-yl)-5-((6-(ethylsulfonyl)pyridin-3-yl)oxy)-2-pyridin-2-yl-1H-indole, 1-((5-((6-(ethylsulfonyl)pyridin-3-yl)oxy)-2-pyridin-2-yl-1H-pyrrolo(2,3-b)pyridin-6-yl)methyl)pyrrolidin-2-one, 1-((5-((6-(5-methyl-1,2,4-oxadiazol-3-yl)pyridin-3-yl)oxy)-2-pyridin-2-yl-1H-pyrrolo(2,3-b)pyridin-6-yl)methyl)pyrrolidin-2-one, 1-((5-((6-(methylsulfonyl)pyridin-3-yl)oxy)-2-pyridin-2-yl-1H-pyrrolo(2,3-b)pyridin-6-yl)methyl)pyrrolidin-2-one, 6-(2,6-difluorophenoxy)-5-((6-(ethylsulfonyl)pyridin-3-yl)oxy)-2-pyridin-2-yl-1H-pyrrolo(2,3-b)pyridine, 6-((2-chloropyridin-3-yl)oxy)-5-((6-(ethylsulfonyl)pyridin)-3-yl)oxy)-2-pyridin-2-yl-1H-pyrrolo(2,3-b)pyridine, 3-((5-((6-(ethylsulfonyl)pyridin-3-yl)oxy)-2-pyridin-2-yl-1H-pyrrolo(2,3-b)pyridin-6-yl)oxy)pyridin-2-carbonitrile, 6-(2,6-difluorophenoxy)-5-((6-(ethylsulfonyl)pyridin-3-yl)oxy)-2-pyrazin-2-yl-1H-pyrrolo(2,3-b)pyridine, 6-((2-(difluoromethoxy)pyridin-3-yl)oxy)-5-((6-(ethylsulfonyl)pyridin-3-yl)oxy-2-pyridin-2-yl-1H-pyrrolo(2,3-b)pyridine, 2-((5-((6-(ethylsulfonyl)pyridin-3-yl)oxy)-2-pyridin-2-yl-1H-pyrrolo(2,3-b)pyridin-6-yl)oxy)-3-fluorobenzonitrile or 2-((5-((6-(ethylsulfonyl)pyridin-3-yl)oxy)-2-pyrazin-2-yl-1H-pyrrolo(2,3-b)pyridin-6-yl)oxy)-3-fluorobenzonitrile, or a pharmaceutically acceptable salt thereof, (9) A glucokinase activator comprising a compound or a pharmaceutically acceptable salt of any one of the above (1) to (8), as the active ingredient thereof;

(10) A remedy and/or a prevention for diabetes, comprising a compound or a pharmaceutically acceptable salt of any one of above (1) to (8), as the active ingredient thereof;

(11) A remedy and/or a prevention for obesity, comprising a compound or a pharmaceutically acceptable salt of any one of above (1) to (8), as the active ingredient thereof.

BEST MODE FOR CARRYING OUT THE INVENTION

The meanings of the terms used in this description are described below, and the compounds of the invention are described in more detail hereinunder.

Unless otherwise specifically indicated in this description, the following examples may be mentioned concretely for the following groups.

"Aryl" preferably means a hydrocarbon aromatic ring having from 6 to 14 carbon atoms, including, for example, phenyl, naphthyl, biphenyl, anthryl. Of those, preferred are phenyl, naphthyl and biphenyl; and more preferred is phenyl.

"$C_{1-6}$ alkyl" means a linear or branched alkyl having from 1 to 6 carbon atoms, including, for example, methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl, 1-ethyl-2-methylpropyl.

"$C_{2-6}$ alkenyl" means a linear or branched alkenyl having from 2 to 6 carbon atoms, including, for example, allyl, 2-propenyl, 1-butenyl, 2-butenyl, 2-methyl-2-butenyl, 1-pentenyl.

"$C_{3-7}$ cycloalkyl" concretely includes cyclopropyl, cyclobutyl, cyclopentyl, cyclohexyl, cycloheptyl.

"Halogen" means fluorine, chlorine, bromine, iodine.

"—$(CH_2)_{1-6}$—OH" includes, for example, hydroxymethylene, hydroxyethylene.

"—O—$C_{1-6}$ alkyl" includes, for example, methoxy, ethoxy, propoxy or tert-butoxy.

"—$(CH_2)_{1-6}$—$OC_{1-6}$ alkyl" includes, for example, methoxymethyl, methoxyethyl, propyloxymethyl, isopropyloxymethyl.

"—C(O)-$_{1-6}$ alkyl" includes, for example, acetyl, ethylcarbonyl, isopropylcarbonyl, propylcarbonyl.

"—C(O)O$C_{1-6}$ alkyl" includes, for example, methoxycarbonyl, ethoxycarbonyl, tert-butoxycarbonyl.

"—$(CH_2)_{1-6}$—$NH_2$" includes, for example, aminomethyl, aminoethyl, aminopropyl.

"—NH—$C_{1-6}$ alkyl" includes, for example, methylamino, ethylamino, propylamino, 2-methylbutylamino.

"—N-di-($C_{1-6}$ alkyl)" means a group composed of the above-mentioned, same or different "$C_{1-6}$ alkyls" and N bonding to each other, and includes, for example, dimethylamino, ethylpropylamino, 2-methylbutyl-1-methylamino. The same or different $C_{1-4}$ alkyls in "—N-di-($C_{1-6}$ alkyl)", taken together with the nitrogen atom, may form a ring. Examples of the ring are piperidine, pyrrolidine.

"—$CH_{3-a}F_a$" means a group of methyl in which from 1 to 3 hydrogen atoms are substituted with a fluorine atom, and includes, for example, trifluoromethyl, difluoromethyl or fluoromethyl.

"—$OCH_{3-a}F_a$" means a group composed of the above-defined "—$CH_{3-a}F_a$" and an oxygen atom bonding to each other, and includes, for example, trifluoromethoxy, difluoromethoxy or fluoromethoxy.

a indicates an integer of from 1 to 3.

For further more concretely disclosing the compounds of the invention of formula (I):

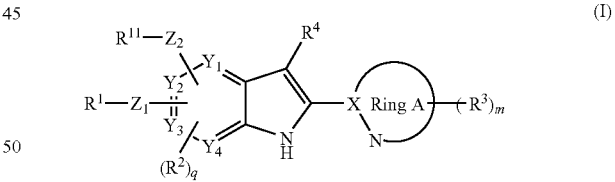

(I)

[wherein the symbols have the same meanings as above], the symbols used in the formula (I) are described with reference to their concrete examples.

$R^1$ represents aryl or heteroaryl having from 1 to 3 hetero atoms selected from the group consisting of a nitrogen atom, a sulfur atom and an oxygen atom.

"Aryl" represented by $R^1$ means the same group as the above-defined "aryl", and is, for example, concretely phenyl or naphthyl, preferably phenyl.

As "heteroaryl having from 1 to 3 hetero atoms selected from the group consisting of a nitrogen atom, a sulfur atom and an oxygen atom" represented by $R^1$, for example, concretely preferred is pyridyl, pyrazinyl or pyrimidinyl; more preferred is pyridyl or pyrazinyl.

$Z_1$ represents —O—, —S—, —S(O)— or —S(O)$_2$—.

$Z_1$ is preferably —O—, —S—, —S(O)— or —S(O)$_2$—, more preferably —O—.

$Z_2$ represents —O—, —S—, —S(O)—, —S(O)$_2$—, —CH$_2$—, or a single bond.

Of the group represented by $Z_2$, —CH$_2$— may be substituted with halogen, —C$_{1-6}$ alkyl, hydroxy, cyano or —O—C$_{1-6}$ alkyl.

Halogen for the substituent may be the same group as the above-defined halogen.

—C$_{1-6}$ alkyl for the substituent may be the same group as the above-defined "—C$_{1-6}$ alkyl".

—O—C$_{1-6}$ alkyl for the substituent may be the same group as the above-defined "—O—C$_{1-6}$ alkyl".

$Y_1$ to $Y_4$ are such that at least two of $Y_1$ to $Y_4$ are carbon atoms, and the remainder are a carbon atom or a nitrogen atom.

$Y_1$ to $Y_4$ are preferably such that all of $Y_1$ to $Y_4$ are carbon atoms, or three of $Y_1$ to $Y_4$ are carbon atoms and the remaining one is a nitrogen atom; more preferably all of $Y_1$ to $Y_4$ are carbon atoms, or $Y_1$ to $Y_3$ are carbon atoms and $Y_4$ is a nitrogen atom.

The ring A represents a 5- or 6-membered heteroaryl having from 1 to 3 hetero atoms selected from the group consisting of a nitrogen atom, a sulfur atom and an oxygen atom, represented by a formula (II):

(II)

or represents a condensed group of the 5- or 6-membered heteroaryl with a phenyl ring or a pyridine ring.

X means a carbon atom or a nitrogen atom.

The ring A includes, for example, thiazolyl, imidazolyl, isothiazolyl, thiadiazolyl, oxadiazolyl, triazolyl, oxazolyl, isoxazolyl, pyrazinyl, pyridyl, pyridazinyl, pyrazolyl or pyrimidinyl. Of those, preferred are thiazolyl, thiadiazolyl, isoxazolyl, pyrazinyl, pyridyl, pyridazinyl, triazolyl, pyrazolyl; more preferred are pyridyl, pyrazinyl, thiazolyl, thiazolyl, isoxazolyl, pyrazolyl; and even more preferred are pyridyl, pyrazinyl.

The ring A may have one or two, the same or different substituents of $R^3$.

$R^3$ each independently represents —C$_{1-6}$ alkyl, —(CH$_2$)$_{1-6}$—OH, —C(O)—OC$_{1-6}$ alkyl, —(CH$_2$)$_{1-6}$—OC$_{1-6}$ alkyl, —(CH$_2$)$_{1-6}$—NH$_2$, cyano, —C(O)—C$_{1-6}$ alkyl, halogen, —C$_{2-6}$ alkenyl, —OC$_{1-6}$ alkyl, —COOH or —OH.

"—C$_{1-6}$ alkyl" for $R^3$ has the same meaning as the above-defined "—C$_{1-6}$ alkyl".

"—(CH$_2$)$_{1-6}$—OC$_{1-6}$ alkyl" for $R^3$ has the same meaning as the above-defined "—(CH$_2$)$_{1-6}$—OC$_{1-6}$ alkyl".

"—C(O)—OC$_{1-6}$ alkyl" for $R^3$ has the same meaning as the above-defined "—C(O)—OC$_{1-6}$ alkyl".

"—C(O)—C$_{1-6}$ alkyl" for $R^3$ has the same meaning as the above-defined "—C(O)—C$_{1-6}$ alkyl".

"Halogen" for $R^3$ has the same meaning as the above-defined "halogen".

"—C$_{2-6}$ alkenyl" for $R^3$ has the same meaning as the above-defined "—C$_{2-6}$ alkenyl".

"—OC$_{1-6}$ alkyl" for $R^3$ has the same meaning as the above-defined "—OC$_{1-6}$ alkyl".

"Aryl" for $R^{11}$ has the same meaning as the above-defined "aryl", concretely including, for example, phenyl and naphthyl, and is preferably phenyl.

"5- or 6-membered aliphatic hetero ring having, in the ring, at least one hetero atom selected from the group consisting of a nitrogen atom, a sulfur atom and an oxygen atom" for $R^{11}$ concretely includes, for example, pyrrolidinyl, piperidino, piperidinyl, piperazinyl, morpholino, thiomorpholino, imidazolidinyl, pyrazolidinyl.

The 5- or 6-membered aliphatic hetero ring may be mono to tri-substituted with the same or different substituents of —C$_{1-6}$ alkyl, —O—C$_{1-6}$ alkyl (the —C$_{1-6}$ alkyl and —O—C$_{1-6}$ alkyl may be substituted with halogen, —O—C$_{1-6}$ alkyl), hydroxy, oxo or thioxo.

"—C$_{1-6}$ alkyl" for the substituent has the same meaning as the above-defined "—C$_{1-6}$ alkyl".

"—O—C$_{1-6}$ alkyl" for the substituent has the same meaning as the above-defined "—O—C$_{1-6}$ alkyl".

"Halogen" for the substituent has the same meaning as the above-defined "halogen".

"—O—C$_{1-6}$ alkyl" for the substituent has the same meaning as the above-defined "—O—C$_{1-6}$ alkyl".

The —C$_{1-6}$ alkyl and —O—C$_{1-6}$ alkyl may be mono to tri-substituted with the same or different substituents of halogen such as fluorine, chlorine, bromine, or lower alkoxy such as methoxy, ethoxy, isopropoxy, or hydroxy.

From the above, the 5- or 6-membered aliphatic hetero ring optionally mono to tri-substituted with the above-mentioned, same or different substituents and having, in the ring, at least one hetero atom selected from the group consisting of a nitrogen atom, a sulfur atom and an oxygen atom concretely includes, for example, those of a formula (III-1):

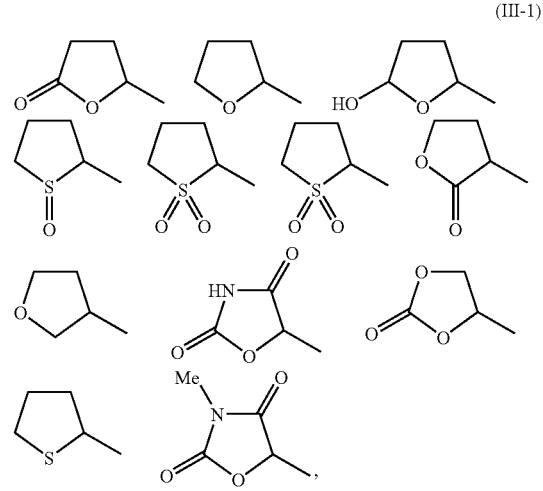

(III-1)

those of a formula (III-2):

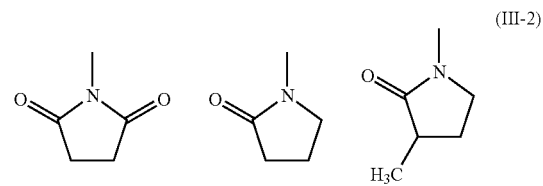

(III-2)

-continued

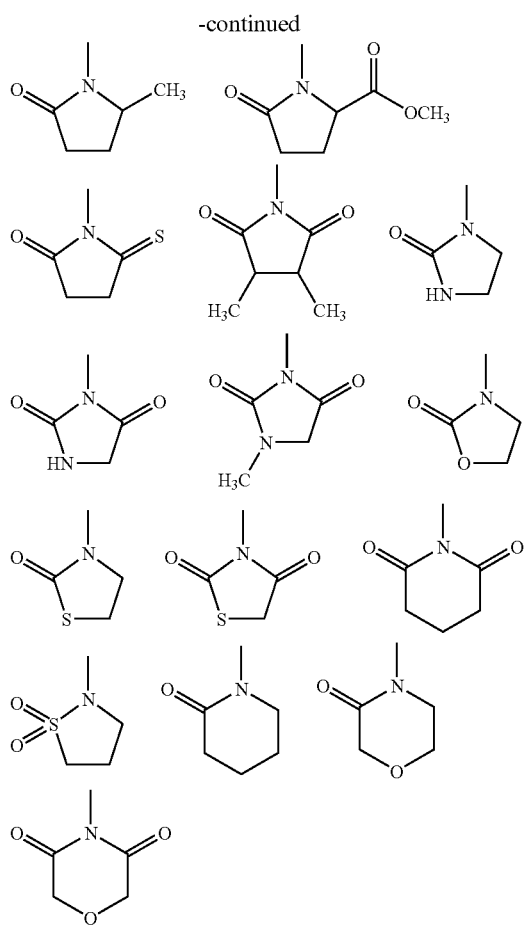

or those of a formula (III-3):

(III-3)

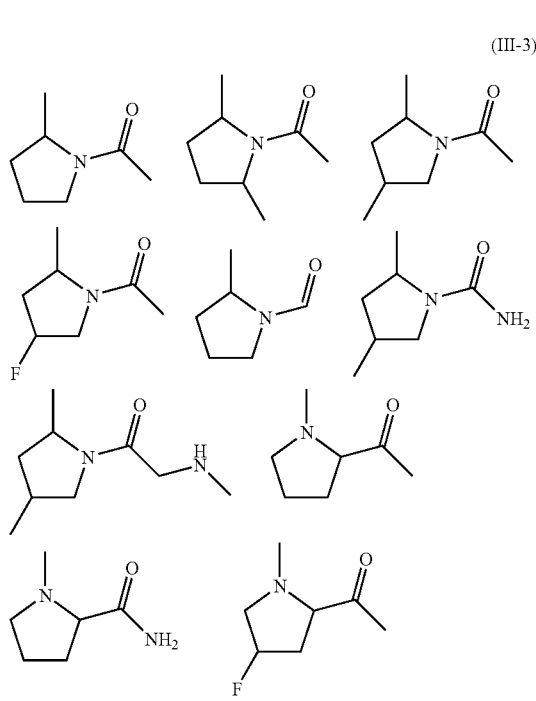

-continued

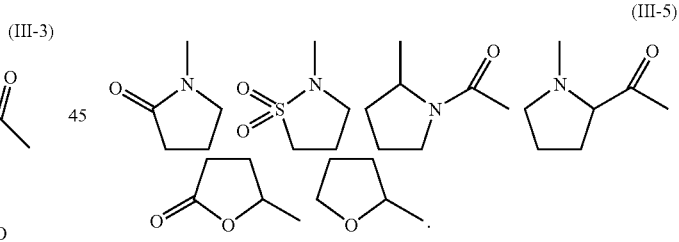

and of those groups, preferred are groups of a formula (III-4):

(III-4)

more preferred are groups of a formula (III-5):

(III-5)

"5- or 6-membered heteroaryl having, in the ring, from 1 to 3 hetero atoms selected from the group consisting of a nitrogen atom, a sulfur atom and an oxygen atom" for $R^{11}$ concretely includes, for example, thienyl, furyl, pyridyl, pyrazinyl.

$R^4$ represents a hydrogen atom or —$C_{1-6}$ alkyl.

"—$C_{1-6}$ alkyl" for $R^4$ means a linear or branched alkyl group having from 1 to 6 carbon atoms, concretely including, for example, methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl, 1-ethyl-2-methylpropyl.

"—$C_{1-6}$ alkyl" for $R^5$ concretely includes the same groups as those of "—$C_{1-6}$ alkyl" for $R^4$.

The "—$C_{1-6}$ alkyl" may be substituted with from 1 to 3 substituents of hydroxy, halogen, —OC(O)—$C_{1-6}$ alkyl (the alkyl may be substituted with from 1 to 3 halogens) or —O—$C_{1-6}$ alkyl.

In case where the "—$C_{1-6}$ alkyl" has 2 or 3, the above-mentioned substituents, they may be the same or different.

Halogen for the substituent includes the same as those of the above-defined halogen.

—OC(O)—$C_{1-6}$ alkyl for the substituent includes, for example, methylcarbonyloxy, ethylcarbonyloxy, isopropylcarbonyloxy.

—OC(O)—$C_{1-6}$ alkyl for the substituent may be mono to tri-substituted with the above-defined halogen atom.

—O—$C_{1-6}$ alkyl for the substituent includes, for example, methoxy, ethoxy, propoxy, isopropoxy.

"—$N(C(O)—R^{51})R^{52}$", for $R^5$ means a substituted or unsubstituted carbamoyl group, or means a group of a 4- to 7-membered aliphatic hetero ring formed by N, $R^{51}$ and $R^{52}$ taken together, with carbonyl bonding thereto.

Of "$C(O)N(R^{51})R^{52}$" for $R^5$, the substituted or unsubstituted carbamoyl includes, for example, carbamoyl, methylcarbamoyl, ethylcarbamoyl, isopropylcarbamoyl, propylcarbamoyl, ethylmethylcarbamoyl, dimethylcarbamoyl, isopropylmethylcarbamoyl, diisopropylcarbamoyl, diethylcarbamoyl.

Of "$C(O)N(R^{51})R^{52}$", for $R^5$, the 4- to 7-membered aliphatic group to be formed by N, $R^{51}$ and $R^{52}$ taken together concretely includes, for example, azetidinyl, pyrrolidinyl, piperidino, piperazinyl, morpholino. Accordingly, $C(O)N(R^{51})R^{52}$ includes azetidine-1-carbonyl, pyrrolidine-1-carbonyl, piperidine-1-carbonyl, piperazine-1-carbonyl, morpholine-1-carbonyl.

"—$S(O)_{0-2}$—$C_{1-6}$ alkyl" for $R^5$ means a group comprising —$S(O)_{0-2}$— and the above-defined —$C_{1-6}$ alkyl bonding thereto, and includes, for example, —S-ethyl, —S-methyl, —S-isopropyl, —S-propyl, —$S(O)_2$-methyl, —$S(O)_2$-ethyl.

—$C_{1-6}$ alkyl in the "—$S(O)_{0-2}$—$C_{1-6}$ alkyl" may be substituted with hydroxy.

"—$(CH_2)_{0-4}$—$N(R^{53})$—$C(O)$—$R^{54}$" in which $R^{53}$ is a hydrogen atom or —$C_{1-6}$ alkyl, and $R^{54}$ is —$C_{1-6}$ alkyl concretely includes, for example, —$CH_2$—NH—C(O)-methyl, —$CH_2$—NH—C(O)-ethyl, —$CH_2$—NH—C(O)-isopropyl, —$CH_2$—NH—C(O)-propyl, —$CH_2$—N(methyl)-C(O)-methyl, —$CH_2$—N(ethyl)-C(O)-methyl, —NH—C(O)-methyl, —NH—C(O)-ethyl, —NH—C(O)-isopropyl, —NH—C(O)-propyl, —N(methyl)-C(O)-methyl, —N(ethyl)-C(O)-methyl.

"—$(CH_2)_{0-4}$—$N(R^{53})$—$C(O)$—$R^{54}$ in which —N—C(O)— and $C_{1-6}$-alkyl of $R^{53}$ and $R^{54}$, taken together, form a 4- to 7-membered nitrogen-containing aliphatic hetero ring (the hetero ring may be substituted with oxo, and may have 1 or 2 double bonds in the ring) concretely includes, for example, groups of a formula (IV):

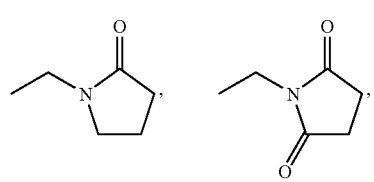

(IV)

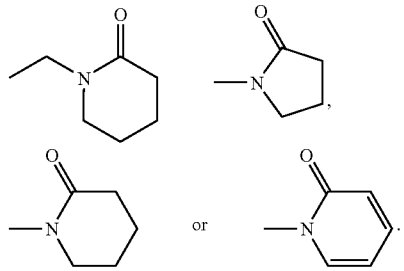

In "—$N(R^{55})$—$C(O)$—$O$—$R^{56}$" for $R^5$, $R^{55}$ means a hydrogen atom or —$C_{1-6}$ alkyl, and $R^{56}$ means —$C_{1-6}$ alkyl, or —N—C(O)—O— and the alkyls of $R^{55}$ and $R^{56}$, taken together, form a 4- to 7-membered nitrogen-containing aliphatic hetero ring.

"—$N(R^{55})$—$C(O)$—$O$—$R^{56}$" in which $R^{55}$ is a hydrogen atom or —$C_{1-6}$ alkyl and $R^{56}$ is —$C_{1-6}$ alkyl concretely includes, for example, —NH—C(O)—O-methyl, —NH—C(O)—O-ethyl, —NH—C(O)—O-isopropyl, —NH—C(O)—O-propyl, —N(methyl)-C(O)—O-methyl, —N(ethyl)-C(O)—O-methyl.

"—$N(R^{55})$—$C(O)$—$O$—$R^{56}$" in which —N—C(O)—O— and the $C_{1-6}$ alkyls of $R^{55}$ and $R^{56}$, taken together, form a 4- to 7-membered nitrogen-containing aliphatic hetero ring concretely includes, for example groups of a formula (V):

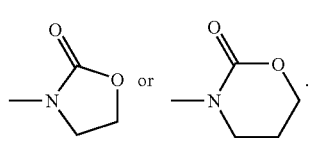

(V)

"—C(O)-aryl" for $R^5$ means a group composed of carbonyl and the above-defined aryl bonding to each other, and concretely it includes, for example, benzoyl, naphthylcarbonyl.

The aryl in "—C(O)-aryl" may be substituted with from 1 to 3, the above-defined halogen atoms.

In case where the group is substituted with 2 or 3 halogen atoms, they may be the same or different.

"—C(O)-aromatic hetero ring" for $R^5$ means a group composed of carbonyl and the above-defined, 5- or 6-membered, monocyclic aromatic hetero ring or 9- or 10-membered bicyclic aromatic hetero ring bonding to each other, and concretely it includes for example, —C(O)-pyrrolyl, —C(O)-furyl, —C(O)-thienyl, —C(O)—, —C(O)-pyrazolyl, —C(O)-isoxazolyl, —C(O)-isothiazolyl, —C(O)-imidazolyl, —C(O)-oxazolyl, —C(O)-thiazolyl, —C(O)-triazolyl, —C(O)-oxadiazolyl, —C(O)-thiadiazolyl, —C(O)-tetrazolyl, —C(O)-pyridyl, —C(O)-pyrazinyl, —C(O)-pyrimidinyl, —C(O)-pyridazinyl.

"—C(O)-aromatic hetero ring" for $R^5$ means a group composed of carbonyl and the above-defined 4- to 7-membered, monocyclic aliphatic hetero ring bonding to each other, and concretely it includes, for example, —C(O)-azetidinyl, —C(O)-pyrrolidinyl, —C(O)-piperidino, —C(O)-piperidinyl, —C(O)-azepanyl, —C(O)-piperazinyl, —C(O)-morpholino, —C(O)-thiomorpholino, —C(O)-homopiperazinyl, —C(O)-imidazolidinyl, —C(O)-pyrazolidinyl.

"Hetero ring" for $R^5$ has the same meaning as that of the ring A.

The hetero ring may be substituted with from 1 to 3 substituents of —$C_{1-6}$-alkyl, halogen or —O—$C_{1-16}$-alkyl.

In case where the group has 2 or 3 substituents, then they may be the same or different.

—$C_{1-6}$ alkyl, halogen and —O—$C_{1-6}$ alkyl for the substituent have the same meanings as those mentioned above.

"Halogen" for $R^5$ has the same meaning as the above-defined "halogen".

"Phenyl" for $R^5$ may be substituted with halogen, —$C_{1-6}$ alkyl or —O—$C_{1-6}$ alkyl.

In case where $R^1$ has 2 or 3 $R^5$'s as the substituents, the same or different two $R^5$'s, taken together, may form a 4- to 6-membered ring, which concretely includes, for example, groups of a formula (VI):

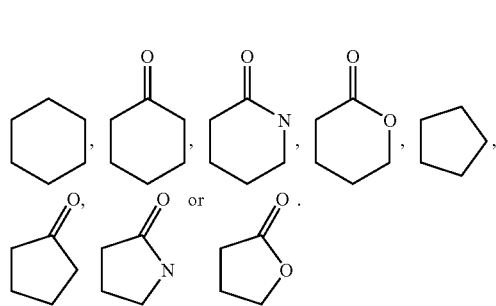
(VI)

$R^2$ each independently represents formyl, —OH, —$C_{1-6}$ alkyl, —$CH_{3-a}F_a$, —$OCH_{3-a}F_a$, amino, cyano, halogen or —$(CH_2)_{1-6}$—OH.

$R^2$ is preferably hydroxy, formyl, —$CH_{3-a}F_a$ (preferably trifluoromethyl), —$OCH_{3-a}F_a$, halogen, —$C_{1-6}$ alkyl, amino, CN, —$(CH_2)_{1-4}OH$; more preferably hydroxy, formyl, —$CH_{3-a}F_a$ (preferably trifluoromethyl), —$OCH_{3-a}F_a$ (preferably trifluoromethoxy), amino, halogen, —$C_{1-6}$ alkyl, CN or —$(CH_2)_{1-4}OH$; even more preferably hydroxy, formyl, amino, halogen (preferably fluorine, chlorine), —$C_{1-6}$ alkyl or —$(CH_2)_{1-4}OH$.

As the above formula (I), preferred are compounds or their pharmaceutically acceptable salts of a formula (I-1):

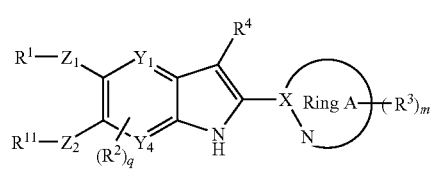
(I-1)

wherein the symbols are the same as above, or compounds or their pharmaceutically acceptable salts of a formula (I-2):

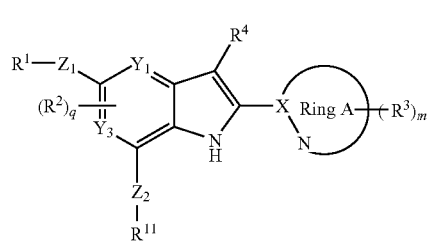
(I-2)

wherein the symbols are the same as above.

The compounds of formula (I) include, for example, compounds of
7-(2-fluorophenoxy)-5-(4-(methylsulfonyl)phenoxy)-2-pyridin-2-yl-1H-indole,
7-(2-fluorophenoxy)-5-(4-(methylsulfonyl)phenoxy)-2-pyrazin-2-yl-1H-indole,
7-(2,6-difluorophenoxy)-5-(4-(methylsulfonyl)phenoxy)-2-pyrazin-2-yl-1H-indole,
7-(2,6-difluorophenoxy)-5-((6-(methylsulfonyl)pyridin-3-yl)oxy)-2-pyridin-2-yl-1H-indole,
7-(2,6-difluorophenoxy)-5-(4-(ethylsulfonyl)phenoxy)-2-pyrazin-2-yl-1H-indole, 7-(2,6-difluorophenoxy)-5-((6-(ethylsulfonyl)pyridin-3-yl)oxy)-2-pyridin-2-yl-1H-indole,
7-(2-cyanophenoxy)-5-((6-(ethylsulfonyl)pyridin-3-yl)oxy)-2-pyridin-2-yl-1H-indole,
2-((5-((6-(methylsulfonyl)pyridin-3-yl)oxy)-2-pyridin-2-yl-1H-indol-6-yl)oxy)-3-fluorobenzonitrile,
2-((5-((6-(ethylsulfonyl)pyridin-3-yl)oxy)-2-pyridin-2-yl-1H-indol-6-yl)oxy)-3-fluorobenzonitrile,
1-methyl-3-((5-(4-methylsulfonyl)phenoxy)-2-pyridin-2-yl-1H-indol-7-yl)oxy)pyridin-2(1H)-one,
1-methyl-3-((5-(4-ethylsulfonyl)phenoxy)-2-pyridin-2-yl-1H-indol-7-yl)oxy)pyridin-2(1H)-one,
5-((6-(ethylsulfonyl)pyridin-3-yl)oxy-7-(2-methoxyphenoxy)-2-pyridin-2-yl-1H-indole,
5-((6-(ethylsulfonyl)pyridin-3-yl)oxy-7-((2-methoxypyridin-3-yl)oxy)-2-pyridin-2-yl-1H-indole,
6-((2-(difluoromethoxy)pyridin-3-yl)oxy)-5-((6-(ethylsulfonyl)pyridin-3-yl)oxy)-2-pyridin-2-yl-1H-indole,
6-((2-(difluoromethoxy)pyridin-3-yl)oxy)-5-((6-(ethylsulfonyl)pyridin-3-yl)oxy-2-pyrazin-2-yl-1H-indole,
6-((2-(difluoromethoxy)pyridin-3-yl)oxy)-5-(4-(ethylsulfonyl)phenoxy)-2-pyridin-2-yl-1H-indole,
6-((2-(difluoromethoxy)pyridin-3-yl)oxy)-5-((6-(methylsulfonyl)pyridin-3-yl)oxy-2-pyridin-2-yl-1H-indole,
6-((2-chloropyridin-3-yl)oxy)-5-((6-(ethylsulfonyl)pyridin-3-yl)oxy-2-pyridin-2-yl-1H-indole,
3-((5-((6-(ethylsulfonyl)pyridin-3-yl)oxy)-2-pyridin-2-yl-1H-indol-6-yl)oxy)pyridin-2-carbonitrile,
6-(2,6-difluorophenoxy)-5e-((6-(ethylsulfonyl)pyridin-3-yl)oxy)-2-pyrazin-2-yl-1H-indole,
6-(2,6-difluorophenoxy)-5e-((6-(ethylsulfonyl)pyridin-3-yl)oxy)-2-pyridin-2-yl-1H-indole,
6-(2,6-difluorophenoxy)-5-((6-(ethylsulfonyl)pyridin-3-yl)oxy)-2-(1-methyl-1H-pyrazol-3-yl)-1H-indole,
6-(2,6-difluorophenoxy)-5-((6-(ethylsulfonyl)pyridin-3-yl)oxy)-2-(1H-pyrazol-3-yl)-1H-indole,
6-(2,6-difluorophenoxy)-5-((6-(ethylsulfonyl)pyridin-3-yl)oxy)-2-(1,2,4-thiadiazol-5-yl)-1H-indole,
6-(2,6-difluorophenoxy)-5-((6-(ethylsulfonyl)pyridin-3-yl)oxy)-2-(1,3-thiadiazol-2-yl)-1H-indole,
2-((5-(4-(methylsulfonyl)phenoxy)-2-pyridin-2-yl-1H-indol-6-yl)oxy)benzamide,
4-((6-(2-aminocarbonyl)phenoxy)-2-pyridin-2-yl-1H-indol-5-yl)oxy)-N,N-dimethylbenzamide,
2-((5-((6-(ethylsulfonyl)pyridin-3-yl)oxy)-2-pyridin-2-yl-1H-indol-6-yl)oxy)benzonitrile,
2-((5-((6-(ethylsulfonyl)pyridin-3-yl)oxy)-2-pyrazin-2-yl-1H-indol-6-yl)oxy)benzonitrile,
5-((6-(ethylsulfonyl)pyridin-3-yl)oxy-6-((2-methoxypyridin-3-yl)oxy)-2-pyridin-2-yl-1H-indole,
5-((6-(ethylsulfonyl)pyridin-3-yl)oxy-6-(2-methoxyphenoxy)-2-pyridin-2-yl-1H-indole,
1-((5-((6-(methylsulfonyl)pyridin-3-yl)oxy)-2-pyridin-2-yl-1H-indol-6-yl)methyl)pyrrolidin-2-one, 1-((5-(((6-(5-methyl-1,2,4-oxadiazol-3-yl)pyridin-3-yl)oxy)-2-pyridin-2-yl-1H-indol-6-yl)methyl)pyrrolidin-2-one, 1-((3-methyl-5-((6-(methylsulfonyl)pyridin-3-yl)oxy)-2-pyridin-2-yl-1H-indol-6-yl)methyl)pyrrolidin-2-one, 1-((5-((6-(methylsulfonyl)pyridin-3-yl)oxy)-2-pyrazin-2-yl-1H-indol-6-yl)methyl)pyrrolidin-2-one, 1-((5-((6-(ethylsulfonyl)pyridin-3-yl)oxy)-2-pyridin-2-yl-1H-indol-6-yl)methyl)pyrrolidin-2-one, 1-((5-(4-(ethylsulfonyl)phenoxy)-2-pyridin-2-yl-1H-indol-6-yl)methyl)pyrrolidin-2-one, 1-((5-(4-(5-methyl-1,2,4-oxadiazol-3-yl)phenoxy)-2-pyridin-2-yl-1H-indol-6-yl)methyl)pyrrolidin-2-one, 1-((5-((6-(methoxymethyl)pyridin-3-yl)oxy)-2-pyrazin-2-yl-1H-indol-6-yl)methyl)pyrrolidin-2-one, 1-((5-((6-(methoxymethyl)pyridin-3-yl)oxy)-2-pyridin-2-yl-1H-indol-6-yl)methyl)pyrrolidin-2-one, 5-(4-methylsulfonyl)phenoxy)-6-((1-methyl)-1H-tetrazol-5-yl)methyl)-2-pyridin-2-yl-1H-indole, 3-((5-((6-ethylsulfonyl)pyridin-3-yl)oxy)-2-pyridin-2-yl-1H-indol-6-yl)methyl)-1,3-oxazolidin-2-one, 3-((5-((6-ethylsulfonyl)pyridin-3-yl)oxy)-2-pyridin-2-yl-1H-indol-6-yl)methyl)-1,3-thiazolidin-2-one, 6-(1-acetylpyrrolidin-2-yl)-5-((6-(ethylsulfonyl)pyridin-3-yl)oxy)-2-pyridin-2-yl-1H-indole, 1-((5-((6-(ethylsulfonyl)pyridin-3-yl)oxy)-2-pyridin-2-yl-1H-pyrrolo(2,3-b)pyridin-6-yl)methyl)pyrrolidin-2-one, 1-((5-((6-(5-methyl-1,2,4-oxadiazol-3-yl)pyridin-3-yl)oxy)-2-pyridin-2-yl-1H-pyrrolo(2,3-b)pyridin-6-yl)methyl)pyrrolidin-2-one, 1-((5-((6-(methylsulfonyl)pyridin-3-yl)oxy)-2-pyridin-2-yl-1H-pyrrolo[2,3-b]pyridin-6-yl)methyl)pyrrolidin-2-one, 6-(2,6-difluorophenoxy)-5-((6-(ethylsulfonyl)pyridin-3-yl)oxy)-2-pyridin-2-yl-1H-pyrrolo(2,3-b)pyridine, 6-((2-chloropyridin-3-yl)oxy)-5-((6-(ethylsulfonyl)pyridin)-3-yl)oxy)-2-pyridin-2-yl-1H-pyrrolo(2,3-b)pyridine, 3-((5-((6-(ethylsulfonyl)pyridin-3-yl)oxy)-2-pyridin-2-yl-1H-pyrrolo(2,3-b)pyridin-6-yl)oxy)pyridin-2-carbonitrile, 6-(2,6-difluorophenoxy)-5-((6-(ethylsulfonyl)pyridin-3-yl)oxy)-2-pyrazin-2-yl-1H-pyrrolo(2,3-b)pyridine, 6-((2-(difluoromethoxy)pyridin-3-yl)oxy)-5-((6-(ethylsulfonyl)pyridin-3-yl)oxy-2-pyridin-2-yl-1H-pyrrolo(2,3-b)pyridine, 2-((5-((6-(ethylsulfonyl)pyridin-3-yl)oxy)-2-pyridin-2-yl-1H-pyrrolo(2,3-b)pyridin-6-yl)oxy)-3-fluorobenzonitrile or 2-((5-((6-(ethylsulfonyl)pyridin-3-yl)oxy)-2-pyrazin-2-yl-1H-pyrrolo(2,3-b)pyridin-6-yl)oxy)-3-fluorobenzonitrile, or their pharmaceutically acceptable salts.

A method for producing a compound according to the invention is described.

Of compounds (1) of the invention, those of formula (I-1) may be produced, for example, according to the following methods:

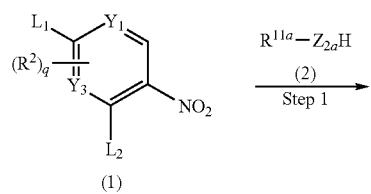

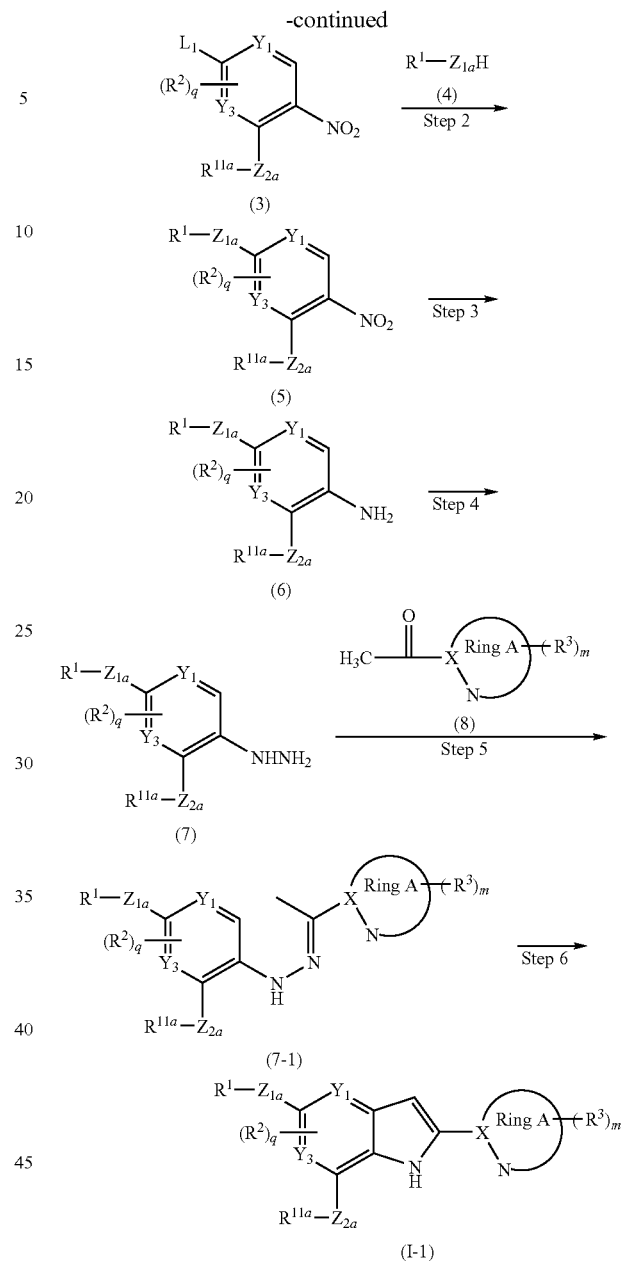

[wherein $Z_{1a}$ and $Z_{2a}$ each independently represent an oxygen atom or a sulfur atom; $R^{11a}$ represents an aryl group, or a 5- or 6-membered heteroaryl group selected from the group consisting of a nitrogen atom, a sulfur atom and an oxygen atom; $L_1$ and $L_2$ each independently represent a leaving group].

(Step 1)

This step is a method for producing a compound (3) by reacting a nitrobenzene derivative (1) having two leaving groups $L_1$ and $L_2$ with a compound (2) $R^{11}$-$Z_{2a}$H in the presence of a base.

$L_1$ may be any one that leaves in the reaction with a compound (4) in the step 2 to produce a compound (5). For example, it includes a halogen atom such as a fluorine atom, a chlorine atom.

L₂ may be any one that leaves in the reaction with a compound (2) in the step 1 to produce a compound (3). For example, it includes a halogen atom such as a fluorine atom, a chlorine atom.

The compound (2) to be used in this step includes, for example, 4-methylsulfonylphenol, 4-ethylsulfonylphenol, 6-methylsulfonyl-3-pyridinol, 6-ethylsulfonyl-3-pyridinol, 6-(5-methyl-1,2,4-oxadiazol-3-yl)-3-pyridinol, 4-cyanophenol, 6-cyano-3-pyridinol, 2,6-difluorophenol, o-fluorophenol, 2-difluoromethoxy-pyridin-3-ol.

The amount of the compound (2) to be used may be generally from 0.5 to 20 equivalents relative to 1 equivalent of the compound (1), preferably from 0.5 to 5 equivalents.

The base to be used in this step includes potassium carbonate, cesium carbonate, potassium phosphate, potassium acetate, sodium hydride, triethylamine, potassium tert-butyrate.

The amount of the base to be used may be generally from 0.5 to 20 equivalents relative to 1 equivalent of the compound (1), preferably from 0.5 to 5 equivalents.

The reaction temperature may be generally from 0° C. to the reflux temperature of the reaction solvent, preferably from 0 to 180° C.

The reaction time may be generally from 0.1 to 72 hours, preferably from 0.1 to 5 hours.

Not specifically defined, the reaction solvent may be any one not interfering with the reaction, and for example, it includes pyridine, toluene, tetrahydrofuran, 1,4-dioxane, N,N-dimethylformamide, N,N-dimethylacetamide, dimethyl sulfoxide, 1-methyl-2-pyrrolidinone, acetonitrile. Of those, preferred is tetrahydrofuran.

The compound (3) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 2)

This step is a method for producing a compound (5) by reacting the compound (3 obtained in the above step 1 with a compound (4) R1-Z1aH in the presence of a base.

The base to be used may be the same as that used in the above step 1.

The compound (4) to be used in this step includes, for example, 4-methylsulfonylphenol, 4-ethylsulfonylphenol, 6-methylsulfonyl-3-pyridinol, 6-ethylsulfonyl-3-pyridinol, 6-(5-methyl-1,2,4-oxadiazol-3-yl)-3-pyridinol, 4-cyanophenol, 6-cyano-3-pyridinol, 2,6-difluorophenol, o-fluorophenol, 2-difluoromethoxy-pyridin-3-ol.

The amount of the compound (4) to be used may be generally from 0.1 to 20 equivalents relative to 1 equivalent of the compound (3), preferably from 0.1 to 5 equivalents.

Not specifically defined, the reaction solvent may be any one not interfering with the reaction, and includes, for example, pyridine, toluene, tetrahydrofuran, 1,4-dioxane, N,N-dimethylformamide, N,N-dimethylacetamide, dimethyl sulfoxide, 1-methyl-2-pyrrolidinone, acetonitrile. Of those, preferred is N,N-dimethylformamide.

The reaction temperature may be generally from 0° C. to the reflux temperature of the reaction solvent, preferably from 0 to 180° C.

The reaction time may be generally from 0.1 to 72 hours, preferably from 0.1 to 5 hours. The compound (5) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 3)

This step is a method for producing a compound (6) by converting the nitro group of the above compound (5) into an amino group.

The reaction in this step may be attained by reacting the compound with a metal catalyst in a hydrogen atmosphere.

The metal catalyst to be used in this step includes, for example, palladium, platinum, Raney nickel.

The amount of the metal catalyst to be used may be generally from 0.1 to 1 equivalent relative to 1 equivalent of the compound (5), preferably from 0.1 to 0.5 equivalents.

Not specifically defined, the reaction solvent may be any one not interfering with the reaction, and includes, for example, methanol, ethanol, N,N-dimethylformamide, ethyl acetate, tetrahydrofuran, and their mixed solvents. Of those, preferred is methanol.

The reaction temperature may be generally from −10 to 100° C., preferably from 0 to 50° C.

The reaction time may be generally from 1 to 24 hours, preferably from 1 to 5 hours.

The compound (6) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 4)

This step is a method for producing a compound (7) by converting the amino group of the above compound (6) into a diazonium salt and reducing it.

The reaction in this step may be attained by reacting the compound (6) with sodium nitrite in the presence of an acid, and adding a reducing agent thereto.

The acid to be used is, for example, concentrated hydrochloric acid.

The amount of the acid to be used may be generally from 1 equivalent to a solvent amount relative to 1 equivalent of the compound (6), preferably from 1 to 100 equivalent.

The amount of sodium nitrite to be used may be generally from 1 to 5 equivalents relative to 1 equivalent of the compound (6), preferably from 1 to 1.5 equivalents.

The reducing agent to be used includes, for example, sulfites and tin(II) chloride dihydrate. Of those, preferred is tin(II) chloride dihydrate.

The amount of the reducing agent to be used may be generally from 1 to 100 equivalents relative to 1 equivalent of the compound (6), preferably from 1 to 5 equivalents.

Not specifically defined, the reaction solvent may be any one not interfering with the reaction. For example, it includes water, etc., and water is preferred.

The reaction temperature may be generally from −10 to 20° C., preferably from 0 to 10° C.

The reaction time may be generally from 0.1 to 3 hours, preferably from 0.5 to 1 hour.

The compound (7) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 5)

This step is a method for producing a compound (7-1) by reacting the compound (7) and a compound (8).

The compound (8) to be used in this step includes, for example, 2-acetylpyridine, 2-acetylthiazole, acetophenone.

The amount of the compound (8) to be used may be generally from 0.5 to 3 equivalents relative to 1 equivalent of the compound (7), preferably from 0.5 to 1 equivalent.

Not specifically defined, the reaction solvent may be any one not interfering with the reaction, and includes, for example, methanol, ethanol, benzene, toluene. Of those, preferred is ethanol.

The reaction temperature may be generally from 0° C. to the reflux temperature of the reaction solvent, preferably from 0 to 100° C.

The reaction time may be generally from 1 to 72 hours, preferably from 3 to 24 hours.

The compound (7-1) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 6)

This step is a method for producing a compound (1) of the invention, by reacting the compound (7-1) with a Broensted acid or a Lewis acid.

The Broensted acid to be used concretely includes, for example, acetic acid, polyphosphoric acid, hydrochloric acid.

The Lewis acid to be used concretely includes, for example, trifluoroborane/ether complex, zinc chloride.

The amount of the acid to be used may be generally from 0.1 to a solvent amount relative to 1 equivalent of the compound (1), preferably from 0.5 to 100 equivalents.

The reaction solvent may be a solvent to be used in Fischer indol synthesis, including, for example, toluene, xylene, acetic acid.

Depending on the type of the acid used in this step, the reaction may be attained in the absence of a solvent.

The reaction temperature may be generally from 100 to 180° C., preferably from 100 to 180° C.

The reaction time may be generally from 0.5 to 24 hours, preferably from 1 to 24 hours.

In the compound (I-1), when $Z_{1a}$ and/or $Z_{2a}$ are a sulfur atom, then the sulfanyl group may be converted into a sulfenyl group or a sulfonyl group according to an ordinary method.

The compound (I-1) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Compounds (I-2) of the invention may be produced, for example, according to the following method:

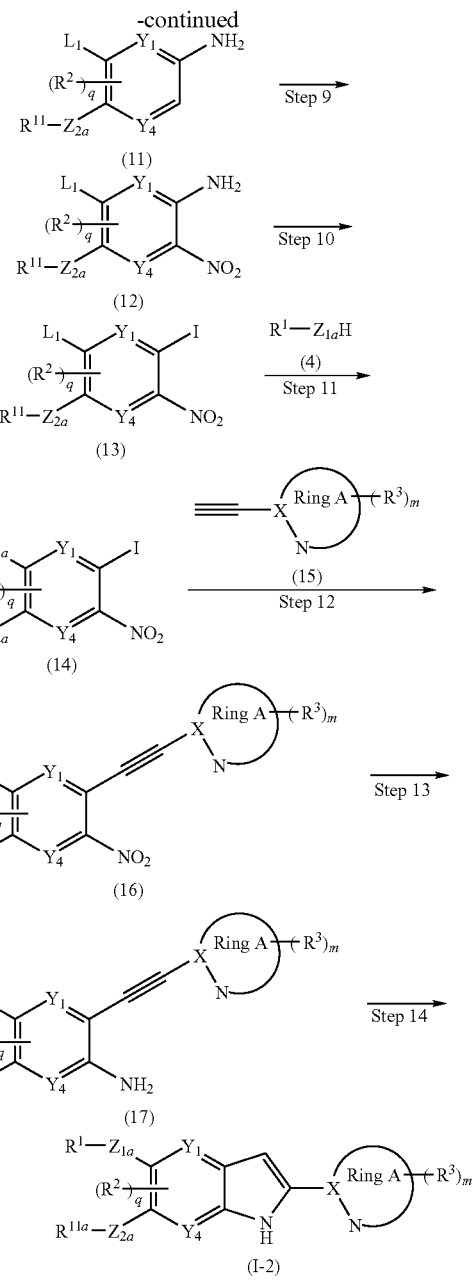

[wherein the symbols are the same as above.]

(Step 7)

This step is a method for producing a compound (10) by reacting a compound (9) with the above-mentioned compound (2) in the presence of a base.

The base to be used in this step includes, for example, cesium carbonate, potassium phosphate, potassium acetate, sodium hydride, potassium tert-butyrate, sodium carbonate, potassium carbonate, triethylamine. The amount of the base to be used may be generally from 0.1 to 20 equivalents relative to 1 equivalent of the compound (9), preferably from 0.5 to 5 equivalents.

Not specifically defined, the reaction solvent maybe any one not interfering with the reaction and includes, for example, pyridine, toluene, tetrahydrofuran, 1,4-dioxane, N,N-dimethylformamide, N,N-dimethylacetamide, dimethyl sulfoxide, 1-methyl-2-pyrrolidinone, acetonitrile. Of those, preferred is acetonitrile.

The reaction temperature may be generally from 0° C. to the reflux temperature of the reaction solvent, preferably from 0 to 180° C.

The reaction time may be generally from 0.1 to 72 hours, preferably from 0.1 to 5 hours.

The compound (10) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 8)

This step is a method for producing a compound (11) by reducing the nitro group of the above compound (10) into an amino group.

The reaction in this step may be attained according to the same method as in the above step 3, or according to a method similar to it, or according to a combination of the method with an ordinary method.

The reduction in this step may be attained, for example, by the use of a Raney nickel as the catalyst in a hydrogen atmosphere.

The compound (11) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 9)

This step is a method for producing a compound (12) by reacting the compound (11) with potassium nitrate in the presence of an acid.

The amount of potassium nitrate to be used in this step may be generally from 1 to 100 equivalents relative to 1 equivalent of the compound (11), preferably from 1 to 5 equivalents.

The acid to be used includes, for example, trifluoroacetic acid, hydrochloric acid, sulfuric acid, nitric acid.

The amount of the acid to be used may be generally from 1 equivalent to a solvent amount relative to 1 equivalent of the compound (11), preferably from 1 to 100 equivalents.

Not specifically defined, the reaction solvent may be any one not interfering with the reaction, including, for example, chloroform, dichloromethane. Of those, preferred is chloroform.

The reaction temperature may be generally from 0° C. to the reflux temperature of the reaction solvent, preferably from 20 to 100° C.

The reaction time may be generally from 0.1 to 72 hours, preferably from 0.5 to 12 hours.

The compound (12) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 10)

This step is a method for producing a compound (13) by converting the amino group of the compound (12) into iodine.

This reaction may be attained by reacting the compound (12) with sodium nitrite under an acid condition, and then with potassium iodide.

The amount of sodium nitrite to be used in this step may be generally from 1 to 5 equivalents relative to 1 equivalent of the compound (12), preferably from 1 to 1.5 equivalents.

The acid to be used includes, for example, hydrochloric acid, sulfuric acid. The amount of potassium iodide to be used may be generally from 1 to 100 equivalents relative to 1 equivalent of the compound (12), preferably from 1 to 20 equivalents.

Not specifically defined, the reaction solvent may be any one not interfering with the reaction, including, for example, tetrahydrofuran, 1,4-dioxane, water. Of those, preferred are water, 1,4-dioxane.

The reaction temperature may be generally from 0 to 100° C., preferably from 0 to 25° C.

The reaction time may be generally from 0.1 to 24 hours, preferably from 0.5 to 5 hours.

The compound (13) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 11)

This step is a method for producing a compound (14) by reacting the compound (13) with a compound (4) $R^1Z_{1a}H$ in the presence of a base.

The base to be used in this step includes, for example, cesium carbonate, potassium phosphate, potassium acetate, sodium hydride, potassium tert-butyrate, triethylamine, sodium carbonate, potassium carbonate.

The amount of the compound (4) to be used may be generally from 0.1 to 20 equivalents relative to 1 equivalent of the compound (3), preferably from 0.1 to 5 equivalents.

The compound (4) includes, for example, 4-methylsulfonylphenol, 4-ethylsulfonylphenol, 6-methylsulfonyl-3-pyridinol, 6-ethylsulfonyl-3-pyridinol, 6-(5-methyl-1,2,4-oxadiazol-3-yl)-3-pyridinol, 4-cyanophenol, 6-cyano-3-pyridinol, 2,6-difluorophenol, o-fluorophenol, 2-difluoromethoxy-pyridin-3-ol.

Not specifically defined, the reaction solvent may be any one not interfering with the reaction, and for example, it includes pyridine, toluene, tetrahydrofuran, 1,4-dioxane, N,N-dimethylformamide, N,N-dimethylacetamide, dimethyl sulfoxide, 1-methyl-2-pyrrolidinone, acetonitrile. Of those, preferred is N,N-dimethylformamide.

The reaction temperature may be generally from 0° C. to the reflux temperature of the reaction solvent, preferably from 0 to 180° C.

The reaction time may be generally from 0.1 to 72 hours, preferably from 0.1 to 5 hours.

The compound (14) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 12)

This step is a method for producing a compound (16) by reacting the compound (14) with a compound (15) in the presence of a base, a palladium catalyst and copper iodide.

The base to be used in this step includes diethylamine, triethylamine, diisopropylethylamine.

The amount of the base may be generally from 1 equivalent to a solvent amount relative to 1 equivalent of the compound (14), preferably from 1 to 100 equivalents.

The palladium catalyst to be used includes, for example, tetrakistriphenylphosphine palladium(0), bis(triphenylphosphine)palladium(II) dichloride complex.

The amount of the palladium catalyst may be generally from 0.01 to 0.5 equivalents relative to 1 equivalent of the compound (14), preferably from 0.01 to 0.2 equivalents.

The amount of copper iodide to be used may be generally from 0.01 to 5 equivalents relative to 1 equivalent of the compound (13), preferably from 0.02 to 1 equivalent.

The compound (15) to be used includes, for example, phenylacetylene, 2-ethynylpyridine.

The amount of the compound (15) to be used may be generally from 0.5 to 20 equivalents relative to 1 equivalent of the compound (14), preferably from 1 to 5 equivalents.

Not specifically defined, the reaction solvent may be any one not interfering with the reaction, including, for example, N,N-dimethylformamide, N,N-dimethylacetamide, toluene, or a solvent may be absent during the reaction. Of those, preferred is N,N-dimethylformamide.

The reaction temperature may be generally from 0° C. to the reflux temperature of the reaction solvent, preferably from 0 to 100° C.

The reaction time may be generally from 0.1 to 72 hours, preferably from 0.5 to 24 hours.

The compound (16) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 13)

This step is a method for producing a compound (17) by reducing the nitro group of the compound (16).

The reducing agent to be used includes, for example, iron, tin(II) chloride, dihydrate.

The amount of the reducing agent may be generally from 1 to 200 equivalents relative to 1 equivalent of the compound (16), preferably from 5 to 100 equivalents.

Not specifically defined, the reaction solvent may be any one not interfering with the reaction, including, for example, methanol, ethanol, N,N-dimethylformamide. Of those, preferred is ethanol.

The reaction temperature may be generally from 0° C. to the reflux temperature of the reaction solvent, preferably from 25 to 100° C.

The reaction time may be generally from 0.1 to 72 hours, preferably from 0.5 to 24 hours.

The compound (17) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 14)

This step is a method for producing a compound (I-2) of the invention by reacting the compound (17) with a strong base.

The strong base to be used in this step includes, for example, palladium(II) chloride, sodium hydride, copper(I) iodide, cesium hydroxide, potassium tert-butoxide.

Not specifically defined, the reaction solvent may be any one not interfering with the reaction, including, for example, toluene, tetrahydrofuran, 1,4-dioxane, N,N-dimethylformamide, N,N-dimethylacetamide, dimethyl sulfoxide, 1-methyl-2-pyrrolidinone. Of those, preferred is 1-methyl-2-pyrrolidinone.

The reaction temperature may be generally from 0° C. to the reflux temperature of the reaction solvent, preferably from 25 to 180° C.

The reaction time may be generally from 0.1 to 240 hours, preferably from 0.5 to 72 hours.

The compound (I-2) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Compounds (I-3) or (I-4) of the invention may be produced, for example, according to the following method.

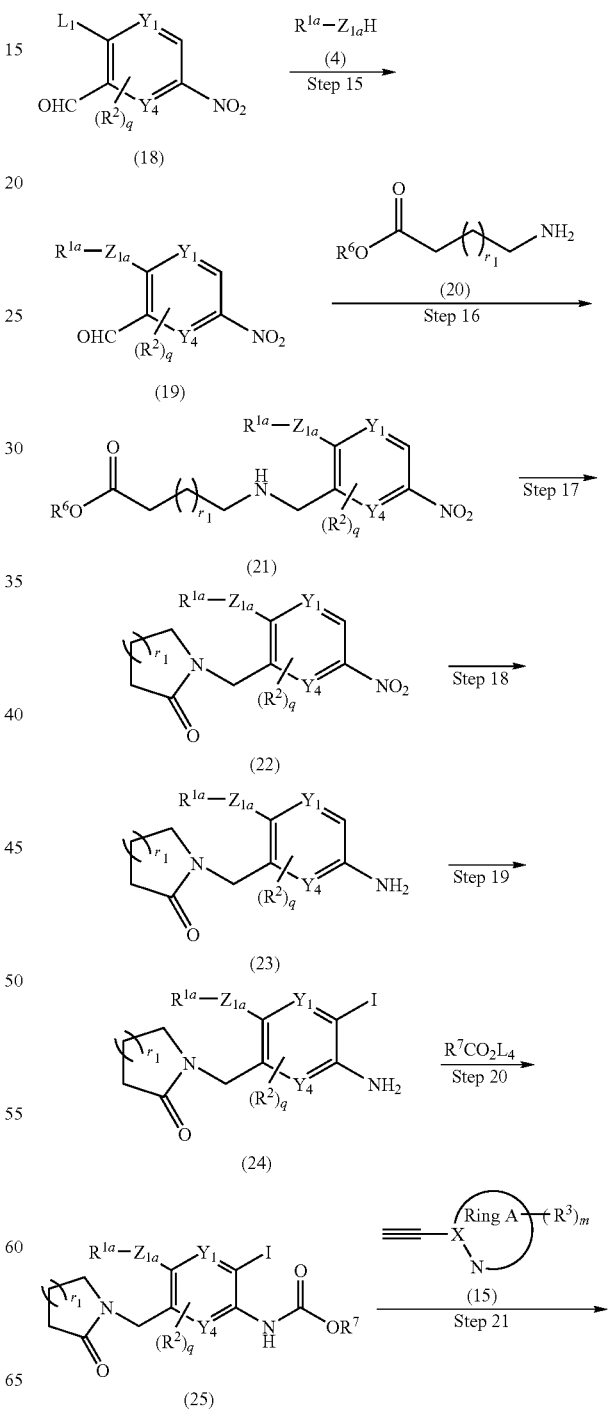

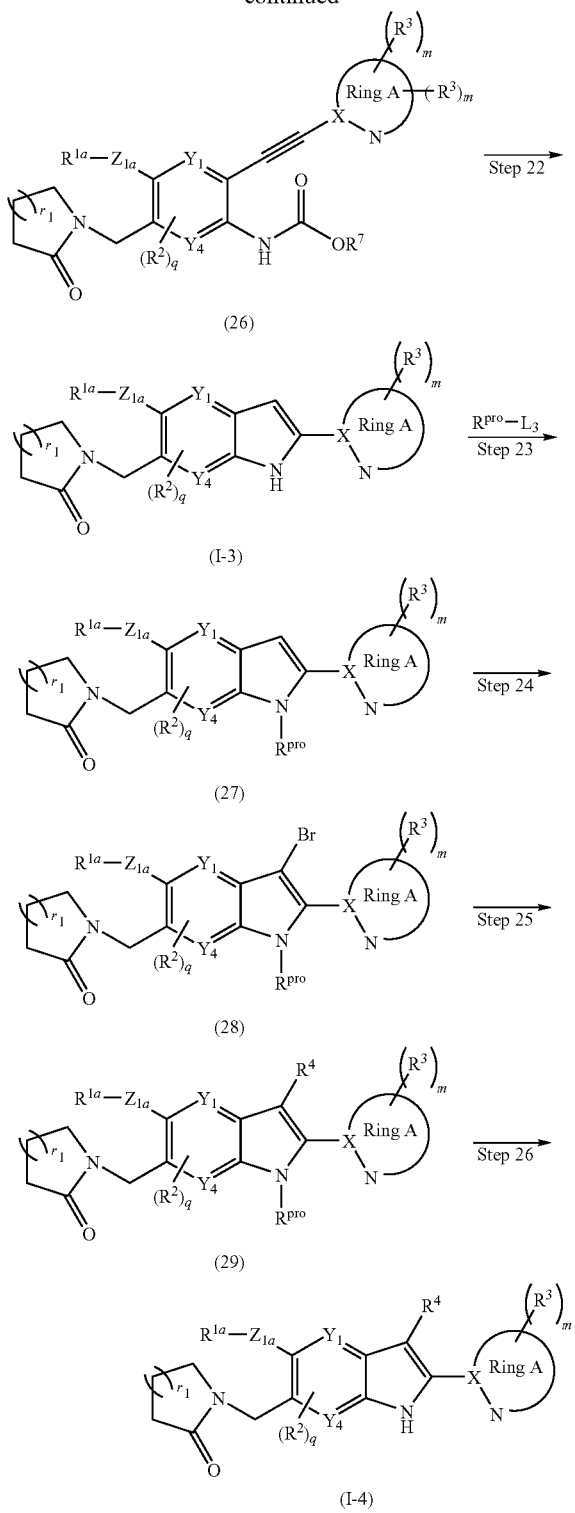

[wherein $r_1$ indicates an integer of from 1 to 3; $R^6$ and $R^7$ each represent $C_{1-6}$ alkyl (the $C_{1-6}$ alkyl may be substituted with from 1 to 3, the same or different halogen atoms); $R^{pro}$ represents a protective group for amino group; $L_3$ and $L_4$ each represent a leaving group; and the other symbols are the same as above.]

(Step 15)

his step is a method for producing a compound (19) by reacting a compound (18) with a compound (4) in the presence of a base.

The compound (18) to be used in this step is, for example, 2-chloro-5-nitrobenzaldehyde.

The base for use in this step includes, for example, potassium phosphate, potassium acetate, sodium hydride, potassium tert-butyrate, cesium carbonate, potassium carbonate, triethylamine.

The amount of the base may be generally from 0.1 to 20 equivalents relative to 1 equivalent of the compound (18), preferably from 0.5 to 5 equivalents.

The compound (4) to be used includes, for example, 4-methylsulfonylphenol, 4-ethylsulfonylphenol, 6-methylsulfonyl-3-pyridinol, 6-ethylsulfonyl-3-pyridinol, 6-(5-methyl-1,2,4-oxadiazol-3-yl)-3-pyridinol, 4-cyanophenol, 6-cyano-3-pyridinol, 2,6-difluorophenol, o-fluorophenol, 2-difluoromethoxy-pyridin-3-ol.

The amount of the compound (4) may be generally from 0.1 to 20 equivalents relative to 1 equivalent of the compound (18), preferably from 0.5 to 5 equivalents.

Not specifically defined, the reaction solvent may be any one not interfering with the reaction, including, for example, pyridine, toluene, tetrahydrofuran, 1,4-dioxane, N,N-dimethylformamide, N,N-dimethylacetamide, dimethyl sulfoxide, 1-methyl-2-pyrrolidinone, acetonitrile. Of those, preferred is 1-methyl-2-pyrrolidinone.

The reaction temperature may be generally from 0° C. to the reflux temperature of the reaction solvent, preferably from 0 to 180° C.

The reaction time may be generally from 0.1 to 72 hours, preferably from 0.1 to 24 hours.

The compound (19) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 16)

This step is a method for producing a compound (21) by reacting the compound (19) with a compound (20).

This reaction is so-called reductive amination, and may be attained according to a method well known to those skilled in the art or according to a method similar to it, or according to a combination of the method with an ordinary method.

The compound (20) to be used in this step includes, for example, methyl 4-aminobutyrate, methyl 5-aminovalerate, methyl 6-aminoheptanoate, or their salts (e.g., hydrochlorides); and the compound (20) may be obtained through esterification of the corresponding carboxylic acid according to a method well known to those skilled in the art, or according to a method similar to it, or according to a combination of the method with an ordinary method.

The amount of the compound (20) to be used may be generally from 1 to 20 equivalents relative to 1 equivalent of the compound (19), preferably from 1 to 5 equivalents.

The reducing agent to be used includes, for example, $NaBH_4$, $Zn(BH_3CN)_2$, $NaB(OAc)_3H$, $NaBH_3CN$, $NaBH_3CN \cdot \frac{1}{2}ZnCl_2$.

The amount of the reducing agent may be generally from 1 to 100 equivalents relative to 1 equivalent of the compound (19), preferably from 1 to 20 equivalents.

In case where a hydrochloride of the compound (20) is used, then a base such as triethylamine may be present in the reaction system.

Not specifically defined, the reaction solvent may be any one not interfering with the reaction, including, for example, methanol, tetrahydrofuran. Of those, preferred is methanol.

The reaction temperature may be generally from 0 to 50° C., preferably from 0 to 30° C.

The reaction time may be generally from 0.1 to 72 hours, preferably from 0.5 to 24 hours.

The compound (21) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 17)

This step is a method for producing a compound (22) by reacting the compound (21) with a base.

The base to be used in this step includes, for example, sodium methoxide, sodium hydroxide, potassium carbonate.

The amount of the base may be generally from 1 to 100 equivalents relative to 1 equivalent of the compound (21), preferably from 1 to 20 equivalents.

Not specifically defined, the reaction solvent may be any one not interfering with the reaction, including, for example, methanol, ethanol, tetrahydrofuran, N,N-dimethylformamide. Of those, preferred is methanol.

The reaction temperature may be generally from 0° C. to the reflux temperature of the reaction solvent, preferably from 0 to 180° C.

The reaction time may be generally from 0.1 to 72 hours, preferably from 0.1 to 24 hours.

The compound (22) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 18)

This step is a method for producing a compound (23) by reducing the nitro group of the compound (22) into an amino group.

This reaction may be attained, for example, by reacting the compound (22) with palladium, platinum or developed Raney nickel catalyst in a hydrogen atmosphere.

The amount of the catalyst to be used may be generally from 0.1 to 1 equivalent relative to 1 equivalent of the compound (22), preferably from 0.1 to 0.5 equivalents.

Not specifically defined, the reaction solvent may be any one not interfering with the reaction, including, for example, methanol, ethanol, N,N-dimethylformamide, ethyl acetate, tetrahydrofuran, and their mixed solvents. Of those, preferred is methanol.

The reaction temperature may be generally from −10 to 100° C., preferably from 1 to 50° C.

The reaction time may be generally from 1 to 24 hours, preferably from 1 to 5 hours.

The compound (23) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 19)

This step is a method for producing a compound (24) by reacting the compound (23) with iodine in the presence of a silver salt.

The silver salt to be used includes, for example, silver nitrate, silver acetate, silver trifluoroacetate, silver carbonate.

The amount of the silver salt to be used may be generally from 1 to 20 equivalents relative to 1 equivalent of the compound (23), preferably from 1 to 5 equivalents.

The amount of iodine to be used may be generally from 0.5 to 10 equivalents relative to 1 equivalent of the compound (23), preferably from 0.5 to 2 equivalents.

Not specifically defined, the reaction solvent may be any one not interfering with the reaction, including, for example, ethanol, acetonitrile, tetrahydrofuran. Of those, preferred is ethanol.

The reaction temperature may be generally from 0° C. to the reflux temperature of the reaction solvent, preferably from 0 to 80° C.

The reaction time may be generally from 0.1 to 72 hours, preferably from 0.1 to 24 hours.

The compound (24) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 20)

This step is a method for producing a compound (25) by reacting the compound (24) with a compound $R^7CO_2L_4$ or its anhydride.

The compound $R^7CO_2L_4$ to be used in this step includes, for example, methyl chloroformate, ethyl chloroformate, isobutyl chloroformate.

The amount of the compound $ClCO_2R^7$ to be used may be generally from 1 to 100 equivalents relative to 1 equivalent of the compound (24), preferably from 1 to 20 equivalent.

Not specifically defined, the reaction solvent may be any one not interfering with the reaction, including, for example, pyridine, N,N-dimethylformamide, tetrahydrofuran, chloroform. Of those, preferred is pyridine.

The reaction temperature may be generally from 0° C. to the reflux temperature of the reaction solvent, preferably from 0 to 100° C.

The reaction time may be generally from 0.1 to 24 hours, preferably from 0.1 to 3 hours.

The compound (25) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 21)

This step is a method for producing a compound (26) by reacting the compound (26) with a compound (15) in the presence of a base, a palladium catalyst and copper iodide.

This reaction may be attained according to the same method as that for the above reaction step 12, or according to a method similar to it, or according to a combination of the method with an ordinary method.

The compound (26) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 22)

This step is a method for producing a compound (I-3) of the invention by reacting the compound (26) with a base.

The base to be used in this reaction includes, for example, tetra(n-butyl)ammonium fluoride, potassium carbonate, potassium tert-butyrate.

The amount of the base to be used in this step may be generally from 1 to 100 equivalents relative to 1 equivalent of the compound (26), preferably from 1 to 10 equivalents.

Not specifically defined, the reaction solvent may be any one not interfering with the reaction, including, for example, pyridine, toluene, tetrahydrofuran, 1,4-dioxane, N,N-dimethylformamide, N,N-dimethylacetamide, dimethyl sulfoxide, 1-methyl-2-pyrrolidinone, acetonitrile. Of those, preferred is tetrahydrofuran.

The reaction temperature may be generally from 0° C. to the reflux temperature of the reaction solvent, preferably from 0 to 180° C.

The reaction time may be generally from 0.1 to 72 hours, preferably from 0.5 to 24 hours.

The compound (I-3) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 23)

This step is a method for producing a compound (27) by reacting the compound (I-3) with a compound $R^{pro}$-$L_3$ in the presence of a base.

This reaction may be attained according to a method described in literature (for example, Protective Groups in Organic Synthesis, by T. W. Green, 2nd Ed., John Wiley & Sons, 1991), or according to a method similar to it, or according to a combination of the method with an ordinary method.

The compound $R^{pro}$-$L_3$ to be used includes, for example, 2-(trimethylsilyl)ethoxymethyl chloride, methoxymethyl chloride.

The amount of the compound $R^{pro}$-$L_3$ to be used may be generally from 1 to 10 equivalents relative to 1 equivalent of the compound (I-3), preferably from 1 to 3 equivalents.

The base to be used is, for example, sodium hydride.

The amount of the base may be generally from 1 to 10 equivalents relative to 1 equivalent of the compound (I-3), preferably from 1 to 3 equivalents.

Not specifically defined, the reaction solvent may be any one not interfering with the reaction, including, for example, N,N-dimethylformamide, tetrahydrofuran, chloroform. Of those, preferred is N,N-dimethylformamide.

The reaction temperature may be generally from –20 to 50° C., preferably from 0 to 25° C.

The reaction time may be generally from 0.1 to 12 hours, preferably from 0.1 to 3 hours.

The compound (27) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 24)

This step is a method for producing a compound (28) by reacting the compound (27) with N-bromosuccinimide.

The amount of N-bromosuccinimide to be used may be generally from 1 to 10 equivalents relative to 1 equivalent of the compound (27), preferably from 1 to 2 equivalents.

Not specifically defined, the reaction solvent may be any one not interfering with the reaction, including, for example, carbon tetrachloride, dichloromethane, chloroform, N,N-dimethylformamide, pyridine. Of those, preferred is dichloromethane.

The reaction temperature may be generally from –10° C. to the reflux temperature of the reaction solvent, preferably from 0 to 50° C.

The reaction time may be generally from 0.1 to 24 hours, preferably from 0.1 to 6 hours.

The compound (28) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 25)

This step is a method for producing a compound (29) by reacting the compound (28) with a dialkylzinc in the presence of a palladium catalyst.

The dialkylzinc to be used in this step may be a commercial product, or may be prepared by reacting an alkyl iodide with zinc according to a method well known to those skilled in the art or according to a method similar to it or according to a combination of the method with an ordinary method.

The dialkylzinc includes, for example, dimethylzinc, diethylzinc, dibutylzinc.

The amount the dialkylzinc to be used in this step may be generally from 0.5 to 10 equivalents relative to 1 equivalent of the compound (28), preferably from 0.5 to 3 equivalents.

The palladium catalyst to be used in this step includes, for example, tetrakistriphenylphosphine palladium(0), bis(triphenylphosphine) palladium(II).

The amount of the palladium catalyst to be used may be generally from 0.01 to 0.5 equivalents relative to 1 equivalent of the compound (28), preferably from 0.01 to 0.2 equivalents.

Not specifically defined, the reaction solvent may be any one not interfering with the reaction, including, for example, tetrahydrofuran, N,N-dimethylformamide, 1,4-dioxane. Of those, preferred is tetrahydrofuran.

The reaction temperature may be generally from 0° C. to the reflux temperature of the reaction solvent, preferably from 0 to 100° C.

The reaction time may be generally from 0.1 to 24 hours, preferably from 0.1 to 5 hours.

The compound (29) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 26)

This step is a method for producing a compound (I-4) of the invention by removing the protective group $R^{pro}$ from the compound (29).

The reaction in this step may be attained according to a method described in literature (for example, Protective Groups in Organic Synthesis, by T. W. Green, 2nd Ed., John Wiley & Sons, 1991), or according to a method similar to it, or according to a combination of the method with an ordinary method.

For example, when the protective group is a 2-(trimethylsilyl)ethoxymethyl group, the compound (29) is reacted with trifluoroacetic acid to remove the protective group $R^{pro}$.

Not specifically defined, the reaction solvent may be any one not interfering with the reaction. For example, it is chloroform.

The reaction temperature may be generally from 0 to 100° C., preferably from 0 to 25° C.

The reaction time may be generally from 0.1 to 24 hours, preferably from 0.5 to 12 hours.

The compound (I-4) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Compound (I-5) of the invention may be produced, for example, according to the following method.

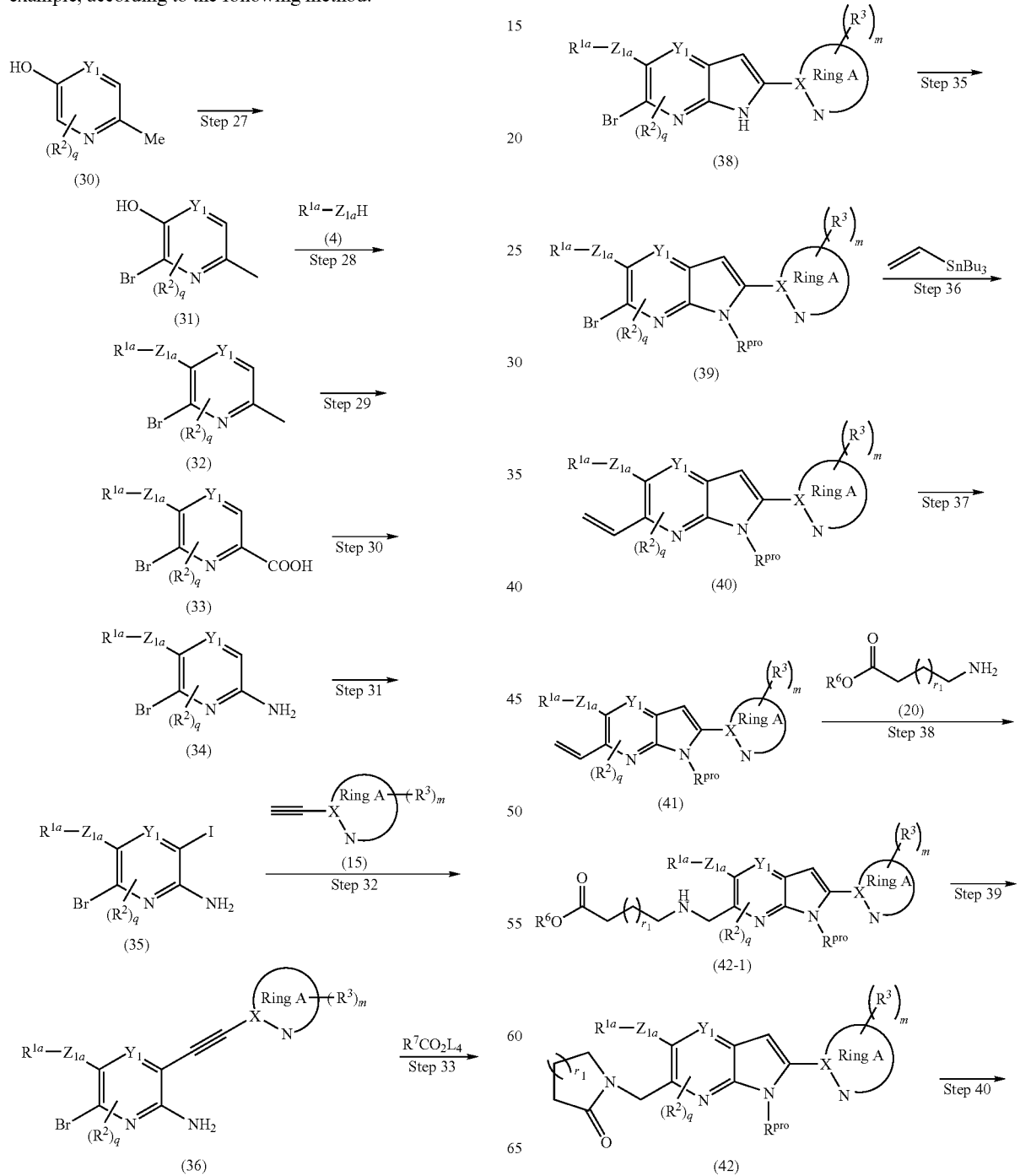

-continued

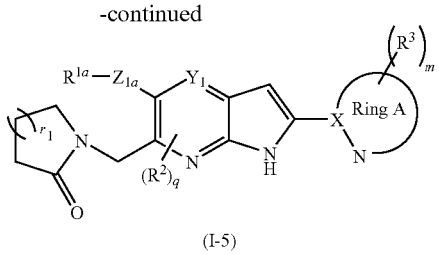

(I-5)

[wherein the symbols are the same as above.]

(Step 27)

This step is a method for producing a compound (31) by reacting a compound (3) with N-bromosuccinimide.

This step may be attained according to the same method as that for the above step 24, or according to a method similar to it, or according to a combination of the method with an ordinary method.

The compound (30) is, for example, 6-methylpyridin-3-ol.

The compound (30) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 28)

This step is a method for producing a compound (32) by reacting the compound (31) with a compound (4) in the presence of a base.

The base to be used in this step includes, for example, potassium phosphate, potassium acetate, sodium hydride, potassium tert-butyrate, cesium carbonate, potassium carbonate, triethylamine.

The amount of the base may be generally from 0.1 to 20 equivalents relative to 1 equivalent of the compound (31), preferably from 0.1 to 5 equivalents.

The amount of the compound (4) may be generally from 0.5 to 20 equivalents relative to 1 equivalent of the compound (31), preferably from 0.5 to 2 equivalents.

Not specifically defined, the reaction solvent may be any one not interfering with the reaction, including, for example, pyridine, toluene, tetrahydrofuran, 1,4-dioxane, N,N-dimethylformamide, N,N-dimethylacetamide, dimethyl sulfoxide, 1-methyl-2-pyrrolidinone, acetonitrile. Of those, preferred is 1-methyl-2-pyrrolidinone.

The reaction temperature may be generally from 0° C. to the reflux temperature of the reaction solvent, preferably from 0 to 180° C.

The reaction time may be generally from 0.1 to 72 hours, preferably from 0.1 to 24 hours.

The compound (32) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 29)

This step is a method for producing a compound (33) by reacting the compound (32) with a nickel catalyst.

The nickel catalyst in this step is, for example, dichloro(bipyridyl)nickel complex.

Dichloro(bipyridyl)nickel complex may be produced according to a method described in literature (e.g., SYNTHETIC COMMUNICATIONS, 1999, Vol. 29, No. 13, p. 2211), or according to a method similar to it, or according to a combination of the method with an ordinary method.

The amount of the nickel catalyst may be generally from 0.01 to 0.5 equivalents relative to 1 equivalent of the compound (32), preferably from 0.01 to 0.3 equivalents.

Not specifically defined, the reaction solvent may be any one not interfering with the reaction, including, for example, acetonitrile, tetrahydrofuran. Of those, preferred is acetonitrile.

The reaction temperature may be generally from 0° C. to the reflux temperature of the reaction solvent, preferably from 0 to 50° C.

The reaction time may be generally from 0.1 to 72 hours, preferably from 0.1 to 24 hours.

The compound (33) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 30)

This step is a method for producing a compound (34) by converting the carboxyl group of the compound (33) into an amino group.

The reaction in this step is a method for producing a compound (34) by reacting a carboxylic acid with diphenylphosphorylazide. This is a modification of Curtius rearrangement by Shioiri, et al., and this may be attained according to a method well known to those skilled in the art.

The amount of diphenylphosphorylazide to be used in this step may be generally from 1 to 10 equivalents relative to 1 equivalent of the compound (33), preferably from 1 to 5 equivalents.

Not specifically defined, the reaction solvent may be any one not interfering with the reaction, including, for example, t-butyl alcohol, toluene, xylene, and their mixed solvents. Of those, preferred is toluene.

The reaction temperature may be generally from 25° C. to the reflux temperature of the reaction solvent, preferably from 50 to 180° C.

The reaction time may be generally from 0.1 to 72 hours, preferably from 0.5 to 24 hours.

The amino group of the compound (33) may be protected with a protective group such as, for example, Boc group, and then may be removed after the reaction.

The introduction and the removal of Boc group may be attained according to a method described in literature (e.g., Protective Groups in Organic Synthesis, by T. W. Green, 2nd Ed., John Wiley & Sons, 1991), or according to a method similar to it, or according to a combination of the method with an ordinary method.

The compound (34) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 31)

This step is a method for producing a compound (35) by reacting the compound (34) with iodine in the presence of a silver salt.

The reaction in this step may be the same as in the above step 19, or may be attained according to a method similar to it, or according to a combination of the method with an ordinary method.

The compound (35) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 32)

This step is a method for producing a compound (36) by reacting the compound (35) with a compound (15) in the presence of a base, a palladium catalyst and copper iodide.

This reaction may be the same as in the above step 12, or may be attained according to a method similar to it, or according to a combination of the method with an ordinary method.

The compound (36) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 33)

This step is a method for producing a compound (37) by reacting the compound (36) with a compound $R^7CO_2L_4$ or its anhydride.

The amount of trifluoroacetic anhydride to be used in this step may be generally from 1 to 50 equivalents relative to 1 equivalent of the compound (36), preferably from 1 to 10 equivalents.

Not specifically defined, the reaction solvent may be any one not interfering with the reaction, including, for example, tetrahydrofuran, chloroform. Of those, preferred is tetrahydrofuran.

The reaction temperature may be generally from 0° C. to the reflux temperature of the reaction solvent, preferably from 0 to 80° C.

The reaction time may be generally from 0.1 to 24 hours, preferably from 0.5 to 6 hours.

The compound (37) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 34)

This step is a method for producing a compound (38) by reacting the compound (34) with a base.

The reaction in this step may be the same as in the above step 14, or may be attained according to a method similar to it, or according to a combination of the method with an ordinary method.

The compound (38) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 35)

This step is a method for producing a compound (39) by reacting the compound (37) with the above-mentioned compound $R^{pro}$-$L_3$ in the presence of a base.

The reaction in this step may be attained according to the same method as in the above step 23, or according to a method similar to it, or according to a combination of the method with an ordinary method.

The compound (39) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 36)

This step is a method for producing a compound (40) by reacting the compound (39) with tri(n-butyl)vinyltin in the presence of a palladium catalyst through Stille coupling reaction.

The palladium catalyst to be used in this step includes, for example, tetrakis(triphenylphosphine)palladium(0), bis (triphenylphosphine)palladium dichloride complex.

The amount of the palladium catalyst may be generally from 0.01 to 0.5 equivalents relative to 1 equivalent of the compound (39), preferably from 0.01 to 0.2 equivalents.

The amount of tri(n-butyl)vinyltin to be used may be generally from 1 to 20 equivalents relative to 1 equivalent of the compound (39), preferably from 1 to 5 equivalents.

Not specifically defined, the reaction solvent may be any one not interfering with the reaction, including, for example, toluene, dioxane, tetrahydrofuran, N,N-dimethylformamide. Of those, preferred is toluene.

The reaction temperature may be generally from 0° C. to the reflux temperature of the reaction solvent, preferably from 25 to 180° C.

The reaction time may be generally from 0.1 to 72 hours, preferably from 0.5 to 24 hours.

The compound (40) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 37)

This step is a method for producing a compound (41) by oxidizing the compound (40).

The oxidizing agent to be used in this step includes, for example, osmium tetroxide, sodium periodate.

The amount of the oxidizing agent may be generally from 0.01 to 50 equivalents relative to 1 equivalent of the compound (40), preferably from 0.01 to 20 equivalents.

Not specifically defined, the reaction solvent may be any one not interfering with the reaction, including, for example, acetone, acetonitrile, t-butyl alcohol, tetrahydrofuran. Of those, preferred is tetrahydrofuran.

The reaction temperature may be generally from 0 to 100° C., preferably from 0 to 50° C.

The reaction time may be generally from 0.1 to 240 hours, preferably from 0.1 to 72 hours.

The compound (41) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 38)

This step is a method for producing a compound (42-1) by reacting the compound (41) with a compound (20).

The reaction in this step may be attained according to the same method as in the above step 16, or according to a method similar to it, or according to a combination of the method with an ordinary method.

The compound (42-1) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 39)

This step is a method for producing a compound (42) by reacting the compound (42-1) with a base.

The reaction in this step may be attained according to the same method as in the above step 17, or according to a method similar to it, or according to a combination of the method with an ordinary method.

The compound (42) thus obtained may be subjected to the next step, after isolated and purified in any known manner for separation and purification, for example, through concentration, concentration under reduced pressure, crystallization, solvent extraction, reprecipitation, chromatography, or not after isolated and purified.

(Step 40)

This step is a method for producing a compound (I-5) of the invention by removing the protective group $R^{pro}$ from the compound (42).

The reaction in this step may be attained according to the same method as in the above step 25, or according to a method similar to it, or according to a combination of the method with an ordinary method.

The compound (I-5) thus obtained may be subjected to the next step, after isolated and purified in any known manner for separation and purification, for example, through concentration, concentration under reduced pressure, crystallization, solvent extraction, reprecipitation, chromatography, or not after isolated and purified.

The acid-addition salts include, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzenesulfonates, p-toluenesulfonates; organic acid salts such as fumarates, succinates, citrates, tartrates, oxalates, maleates; other organic acid-addition salts with amino acid such as glutamates, aspartates. When the compounds of the invention have an acid group in the molecule, for example, when they have a carboxyl group, then the compounds may be processed with a base so as to convert them into the corresponding pharmaceutically acceptable salts. The base-addition salts include, for example, alkali metal salts with sodium or potassium; alkaline earth metal salts with calcium or magnesium; ammonium salts; organic base-addition salts with guanidine, triethylamine, dicyclohexylamine, etc. In addition, the compounds of the invention may also be in any other form of hydrates or solvates of their free compounds or their salts.

In producing medicines for prevention and remedy of type II diabetes or diseases or symptoms associated with it, the compounds of formula (I) of the invention may be used, as combined with carrier substances.

The dose of the compounds of formula (I) of the invention for prevention or remedy of diseases naturally varies, depending on the property of the symptom to be treated, the specific compound selected for it and the administration route.

In addition, the dose also varies depending on the age, the body weight and the sensitivity of patients. In general, the daily dose for one-time or plural-times administration may be from about 0.001 mg/kg-body weight to about 100 mg/kg-body weight, preferably from about 0.01 mg/kg-body weight to about 50 mg/kg-body weight, even more preferably from about 0.1 mg/kg-body weight to about 10 mg/kg-body weight. As the case may be, administration of a dose over the range may be necessary.

An example of a suitable dose for oral administration is described. The daily dose for one-time or two- to four-times administration may be at least from about 0.01 mg to at most 2.0 g. Preferably, the daily administration frequency is once or twice a day, and the daily dose is from about 1.0 mg to about 200 mg. More preferably, the daily dose is from about 10 mg to 100 mg for one-time administration a day.

For intravenous administration or oral administration, a typical dose of the compound (1) may be from about 0.001 mg/day/kg-body weight to about 100 mg/day/kg-body weight (preferably from 0.01 mg/day/kg-body weight to about 10 mg/day/kg-body weight), more preferably from about 0.1 mg/day/kg-body weight to 10 mg/day/kg-body weight.

As so mentioned hereinabove, the pharmaceutical composition of the invention comprises a compound of formula (I) and a pharmaceutically acceptable carrier. The term "composition" is meant to contain not only a product produced by directly or indirectly combining, hybridizing or aggregating 2 or more ingredients, a product produced as a result of dissociation of one or more ingredients, or a compound produced as a result of reaction or interaction of different types of ingredients, but also an active and inactive ingredient of constituting a carrier (pharmaceutically acceptable vehicle).

As combined with a pharmaceutically acceptable carrier, the composition of the invention preferably contains a compound of formula (I) in an amount effective for remedy and prevention of type II diabetes and for retardation of the onset of the disease.

For administering the effective dose of the compound of the invention to mammals, especially to humans, employable is any suitable administration route. For example, the route may be oral administration, rectal administration, local administration, intravenous administration, ophthalmic administration, lung administration or nasal administration. Examples of the administration forms are tablets, troches, powders, suspensions, solutions, capsules, creams, aerosols. Preferred are oral tablets.

In preparing oral compositions, usable are any ordinary pharmaceutical media. Their examples are water, glycol, oil, alcohol, fragrant additives, preservatives, colorants. In preparing liquid compositions for oral administration, for example, mentioned are suspensions, elixirs and solutions. Their carriers are, for example, starch, sugar, microcrystalline cellulose, diluent, granulating promoter, lubricant, binder, disintegrator. In preparing solid compositions for oral administration, for example, mentioned are powders, capsules and tablets. Above all, such solid compositions for oral administration are preferred.

In view of the easiness in their administration, tablets and capsules are the most advantageous forms for oral administration. If desired, the tablets may be coated according to standard aqueous or non-aqueous coating techniques.

In addition to the above-mentioned ordinary administration modes for them, the compounds of formula (I) may also be administered according to controlled release systems and/ or controlled delivery systems, for example, as in U.S. Pat. Nos. 3,845,770, 3,916,899, 3,536,809, 3,598,123, 3,630,200 and 4,008,719.

The pharmaceutical composition of the invention suitable for oral administration includes capsules, cachets and tablets that contain a predetermined amount of the active ingredient in the form of powders or granules thereof, or in the form of water-soluble liquids, water-insoluble liquids, oil-in-water emulsions or water-in-oil emulsions thereof. These compositions may be prepared in any pharmaceutical methods, and all the methods include a process of combining the active ingredient with a carrier of one or more necessary ingredients.

In general, the active ingredient is uniformly and fully mixed with a liquid carrier, or a well-separated solid carrier or with both the two, and then, if desired, the product is shaped into suitable forms to prepare the composition. For example, tablets are produced through compression and shaping, optionally along with one or more side components. Using a suitable machine, compressed tablets may be produced by mixing the active ingredient optionally with binder, lubricant, inert vehicle, surfactant or dispersant and compressing the resulting mix in any desired manner into powders or granules.

Shaped tablets may be prepared by shaping a mixture of a powdery wet compound and an inert liquid diluent, using a suitable machine.

Preferably, the tablets each contain from about 1 mg to 1 g of the active ingredient; and the cachets and the capsules each contain from about 1 mg to 500 mg of the active ingredient.

Examples of the administration modes of the compounds of formula (I) for pharmaceutical use are as follows:

TABLE 1

Suspension for Injection (I.M.)

| | mg/ml |
| --- | --- |
| compound of formula (I) | 10 |
| methyl cellulose | 5.0 |
| Tween 80 | 0.5 |
| benzyl alcohol | 9.0 |
| benzalkonium chloride | 1.0 |
| water for injection added to make 1.0 ml. | |

TABLE 2

Tablets

| | mg/tablet |
| --- | --- |
| compound of formula (I) | 25 |
| methyl cellulose | 415 |
| Tween 80 | 14.0 |
| benzyl alcohol | 43.5 |
| magnesium stearate | 2.5 |
| | total 500 mg |

TABLE 3

Capsules

| | mg/capsule |
| --- | --- |
| compound of formula (I) | 25 |
| lactose powder | 573.5 |
| magnesium stearate | 1.5 |
| | total 600 mg |

TABLE 4

Aerosol

| | per one container |
| --- | --- |
| compound of formula (I) | 24 mg |
| lecithin, NF Liq. Conc. | 1.2 mg |
| trichlorofluoromethane, NF | 4.025 g |
| dichlorodifluoromethane, NF | 12.15 g |

The compounds of formula (I) may be used, as combined with any other drugs usable not only for type II diabetes-associated diseases or symptoms but also for remedy/prevention/retardation of the onset of type II diabetes. The additional drugs may be administered in any administration route and dose generally employed in the art, simultaneously with or separately from the compound of formula (I).

In case where the compound of formula (I) is used along with one or more other medicines, then a pharmaceutical composition comprising the compound of formula (I) and those additional drugs is preferred. Accordingly, the pharmaceutical composition of the invention may comprise not only the compound of formula (I) but also one or more such active ingredients. Examples of the active ingredients that may be combined with the compounds of formula (I) are mentioned below, which, however, are not limitative. These may be separately administered or may be administered simultaneously as contained in the same pharmaceutical composition.

(a) other glucokinase activators,
(b) bis-guanides (e.g., buformin, metoformin, fenformin,),
(c) PPAR agonists (e.g., triglytazon, pioglytazon, nosiglytazon),
(d) insulin,
(e) somatostatin,
(f) α-glucosidase inhibitors (e.g., boglybose, miglytol, acarbose),
(g) insulin secretion promoters (e.g., acetohexamide, calbutamide, chlorpropamide, glybomlide, glycrazide, glymerpide, glypidide, glyquidine, glysoxepide, glyburide, glyhexamide, glypinamide, fenbutamide, trazamide, tolbutamide, tolcyclamide, nateglynide, repaglynide), and
(h) DPP-IV (dipeptidyl peptidase IV) inhibitors.

The weight ratio of the compound of formula (I) to the second active ingredient may vary within a broad range, and depends on the effective amount of the individual active ingredients. Accordingly, for example, when the compound of formula (I) is combined with a PPAR agonist, then the weight ratio of the compound of formula (I) to the PPAR agonist may be generally from about 1000/1 to 1/1000, preferably from about 200/1 to 1/200. The combination of the compound of formula (I) and the other active ingredient may be within the above-mentioned range. In any case, an effective amount of the individual active ingredients should be in the combination.

The glucokinase-activating potency of the compounds of formula (I) of the invention and a test method for it are described below.

The excellent glucokinase-activating effect of the compounds of formula (I) may be determined by a method described in literature (e.g., Diabetes, Vol. 45, pp. 1671-1677, 1996), or in accordance with it.

The glucokinase activity may be determined not by directly measuring glucose-6-phosphate but by measuring the level of Thio-NADH, which is produced when a reporter enzyme, glucose-6-phosphate dehydrogenase produces phosphogluconolactone from glucose-6-phosphate, and based on that level, the level of glucokinase activation may be determined.

In this assay, used was a recombinant human liver GK, which was expressed by *E. coli* as a FLAG fusion protein therein and was purified by ANTIFLAG M2 AFFINITY GEL (Sigma).

Using a flat-bottomed 96-well plate, the assay was carried out at 30° C. 69 µl of an assay buffer (25 mM Hepes Buffer, pH=7.2, 2 mM MgCl$_2$, 1 mM ATP, 0.5 mM TNAD, 1 mM dithiothreitol) was put into the plate, and 1 µl of a DMSO solution of the compound or DMSO alone as a control was added thereto. Next, 20 µl of an enzyme mixture (FLAG-GK, 20 U/ml G6PDH) cooled in ice was added to it, and 10 µl of a substrate, 25 mM glucose was added to it, and the reaction was initiated (final glucose concentration=2.5 mM).

After the start of the reaction, the increase in the absorbance at 405 nm was measured for 12 minutes at intervals of 30 seconds, and the increase for the first 5 minutes was used for evaluating the compound tested. FLAG-GK was added so that the absorbance increase after 5 minutes in the presence of 1% DMSO could be from 0.04 to 0.06.

The OD level of the DMSO control was set as 100%; and the OD level of the test compound at different concentrations was determined. From the OD level at each concentration, Emax (%) and EC50 (µM) were computed and used as the index of the GK-activating potency of the compound.

The GK-activating potency of the compounds of the invention was measured according to the method as above, and the results are shown in Table 5 below.

TABLE 5

| Example No. | Emax (%) | EC50 (µM) |
|---|---|---|
| Example 2 | 1002 | 0.18 |
| Example 3 | 1413 | 0.07 |
| Example 6 | 1322 | 0.05 |

As in the above Table, the compounds of the invention have an excellent GK-activating potency indicated by Emax and EC50.

EXAMPLES

The invention is described more concretely with reference to the following Preparation Examples and Examples, by which, however, the invention should not be limited at all.

Preparation Example 1

10 parts of the compound of Example 1, 15 parts of heavy magnesium oxide and 75 parts of lactose are uniformly mixed to give a powdery or particulate preparation of at most 350 µm in size. The preparation is encapsulated to prepare capsules.

Preparation Example 2

45 parts of the compound of Example 1, 15 parts of starch, 16 parts of lactose, 21 parts of crystalline cellulose, 3 parts of polyvinyl alcohol and 30 parts of distilled water are uniformly mixed, then ground, granulated and dried, and thereafter sieved to prepare granules having a size of from 1410 to 177 µm in diameter.

Preparation Example 3

Granules are prepared in the same manner as in Preparation Example 2. 3 parts of calcium stearate is added to 96 parts of the granules, and shaped under compression to give tablets having a diameter of 10 mm.

Preparation Example 4

10 parts of crystalline cellulose and 3 parts of calcium stearate are added to 90 parts of the granules obtained according to the method of Preparation Example 2, and shaped under compression to give tablets having a diameter of 8 mm. These are coated with a mixture suspension of syrup gelatin and precipitated calcium carbonate to prepare sugar-coated tablets.

In the following, the invention is described more concretely with reference to Preparation Examples, Examples and Reference Examples, by which, however, the invention should not be limited at all.

In the thin-layer chromatography in Examples, Silicagel 60F$_{245}$ (Merck) was used for the plate, and a UV detector was used for detection. For the column silica gel, used was Wakogel™ C-300 (Wako Pure Chemical); and for the reversed-phase column silica gel, used was LC-SORB™ SP-B-ODS (Chemco) or YMC-GEL™ ODS-AQ 120-S50 (Yamamura Chemical Laboratory).

The meanings of the abbreviations in the following Examples are shown below.

i-Bu: isobutyl n-Bu: n-butyl t-Bu: t-butyl

Me: methyl

Et: ethyl

Ph: phenyl i-Pr: isopropyl n-Pr: n-propyl

CDCl$_3$: heavy chloroform

CD$_3$OD: heavy methanol

DMSO-d$_6$: heavy dimethylsulfoxide

The meanings of the abbreviations in nuclear magnetic resonance spectrometry are shown below.

s: singlet d: doublet dd: double-doublet t: triplet m: multiplet br: broad brs: broad singlet q: quartet J: coupling constant Hz: hertz

Example 1

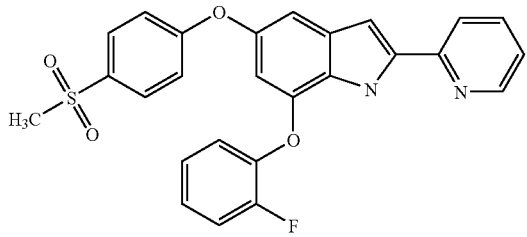

7-(2-Fluorophenoxy)-5-[4-(methylsulfonyl)phenoxy]-2-pyridin-2-yl-1H-indole (Step 1)

Synthesis of 4-fluoro-2-(2-fluorophenoxy)-1-nitrobenzene

With cooling with ice, 377 mg of sodium hydride (30% liquid paraffin added) was added to a tetrahydrofuran solution of 2,4-difluoro-1-nitrobenzene (1 g), and then o-fluorophenol (775 mg) was added, and stirred at room temperature for 2 hours. Water was added, then extracted with ethyl acetate, and the organic layer was washed with saturated saline water. After dried, the solvent was evaporated away under reduced pressure, and the residue was purified by silica gel column chromatography (developing solvent: hexane/ethyl acetate) to obtain the entitled compound.

(Step 2)

Synthesis of 2-(2-fluorophenoxy)-4-[4-(methylsulfonyl)phenoxy]-1-nitrobenzene Potassium carbonate (82.5 mg) was added to an N,N-dimethylformamide (4 ml) solution of the fluorobenzene compound (100 mg) obtained in the step 1 and 4-(methylsulfonyl)phenol (75.4 mg) obtained in Reference Example 1, and stirred at 80° C. for 2 hours. With cooling with ice, water was added, then extracted with ethyl acetate, and the organic layer was washed with saturated saline water. After dried, the solvent was evaporated away under reduced pressure, and the residue was purified by silica gel column chromatography (developing solvent: hexane/ethyl acetate) to obtain the entitled compound.

(Step 3)

Synthesis of 2-(2-fluorophenoxy)-4-[4-(methylsulfonyl)phenoxy]aniline

A developed Raney nickel catalyst was added to a methanol (4 ml)/tetrahydrofuran (1 ml) mixed solution of the nitrobenzene compound (133 mg) obtained in the step 2, and stirred in a hydrogen atmosphere at room temperature for 3 hours. After purging with nitrogen, the insoluble matter was removed by filtration, and the filtrate was concentrated. The residue was dissolved in ethyl acetate, then washed with water and saturated saline water. After dried, the solvent was evaporated away under reduced pressure, and the residue was purified by silica gel column chromatography (developing solvent: hexane/ethyl acetate) to obtain the entitled compound.

(Step 4)

Synthesis of (2-(2-fluorophenoxy)-4-[4-(methylsulfonyl)phenoxy]phenyl)hydrazine With cooling with ice, a water (350 µl) solution of sodium nitride (22.3 mg) was added to a concentrated hydrochloric acid (700 µl)/water (350 µl) suspension of the aniline compound (115 mg) obtained in the step 3, and stirred for 30 minutes. A concentrated hydrochloric acid (700 µl) solution of tin(II) chloride dihydrate (139 mg) was added, and the stirred for 3 hours with gradually heating up to room temperature. After concentrated, this was dissolved in ethyl acetate, and with cooling with ice, aqueous saturated sodium hydrogencarbonate solution was added. The insoluble matter was removed by filtration, the filtrate was washed with aqueous saturated sodium hydrogencarbonate solution and saturated saline water. After dried, the solvent was evaporated away under reduced pressure, and the residue was purified by silica gel column chromatography (developing solvent: hexane/ethyl acetate) to obtain the entitled compound.

(Step 5)

Synthesis of (1E)-1-pyridin-2-ylethanone(2-(2-fluorophenoxy)-4-[4-(methylsulfonyl)phenoxy]phenyl)hydrazone Acetic acid (10 µl) was added to an ethanol (1 ml) solution of the hydrazine compound (76 mg) obtained in the step 4 and 2-acetylpyridine (24 mg), and heated overnight under reflux. After concentrated, this was diluted with ethyl acetate, washed with aqueous saturated sodium hydrogencarbonate solution and saturated saline water. After dried, the solvent was evaporated away under reduced pressure, and the residue was purified by partitioning thin-layer chromatography (Kieselgel™ 60F254, Art 5744 (by Merck), chloroform/methanol=10/1) to obtain the entitled compound.

(Step 6)

Synthesis of 7-(2-fluorophenoxy)-5-[4-(methylsulfonyl)phenoxy]-2-pyridin-2-yl-1H-indole An acetic acid (1 ml) solution of the hydrazone compound (46 mg) obtained in the step 5 was stirred at 100° C. for 6 hours. Further, trifluoroborane/ether complex (40 µl) was added, then stirred overnight at 110° C. With cooling with ice, this was diluted with ethyl acetate, neutralized with aqueous saturated sodium hydrogencarbonate solution, then the organic layer was washed with aqueous saturated sodium hydrogencarbonate solution and saturated saline water. After dried, the solvent was evaporated away under reduced pressure, and the residue was purified by partitioning reversed-phase liquid chromatography to obtain the entitled compound.

1H-NMR (CDCl$_3$) δ: 3.05 (3H, s), 6.37-6.38 (1H, m), 6.98-7.09 (3H, m), 7.11-7.26 (6H, m), 7.74-7.80 (1H, m), 7.81-7.87 (3H, m), 8.61-8.64 (1H, m), 9.88 (1H, brs).

ESI-MASS (m/e): 475[M+H]

Example 2

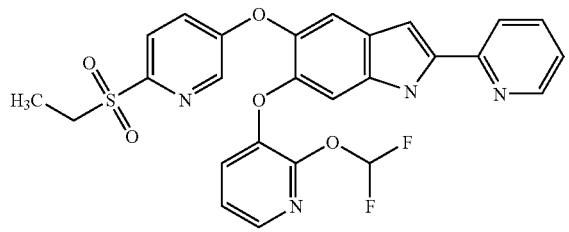

6-([2-(Difluoromethoxy)pyridin-3-yl]oxy)-5-([6-(ethylsulfonyl)pyridin-3-yl]oxy)-2-pyridin-2-yl-1H-indole (Step 1)

Synthesis of 2-difluoromethoxy-pyridin-3-ol

Sodium carbonate (2.1 g) and difluorofluorosulfonylacetic acid (1.24 ml) were added to an acetonitrile (40 ml) suspension of 3-benzyloxy-2-hydroxypyridine (2 g), and the reaction solution was stirred at room temperature for 1 hour, then the solvent was evaporated away under reduced pressure. The residue was diluted with ethyl acetate, washed with water, and dried over anhydrous magnesium sulfate. The solvent was evaporated away under reduced pressure, and the obtained residue was purified by silica gel column chromatography (developing solvent: hexane/ethyl acetate=9/1 to 4/1) to obtain a difluoromethoxy compound (2.39 g) as a pale yellow oily substance.

10% palladium-carbon catalyst (500 mg) was added to a methanol (25 ml) solution of the difluoromethoxy compound (2.38 g), and the reaction solution was stirred in a hydrogen atmosphere at room temperature for 1 hour. The catalyst was removed by filtration through Celite, and the solvent was evaporated away under reduced pressure to obtain the entitled compound as a pale violet oily substance.

(Step 2)

Synthesis of 2-(difluoromethoxy)-3-(2-fluoro-4-nitrophenoxy)pyridine

Potassium carbonate (3.6 g) was added to an acetonitrile (30 ml) solution of 2-(difluoromethoxy)pyridin-3-ol (2.3 g) obtained in the step 1 and 3,5-difluoronitrobenzene (1.9 g), and stirred at 80° C. for 1 hour. The solvent was evaporated away under reduced pressure, then water was added, and extracted with ethyl acetate. After dried, the solvent was evaporated away under reduced pressure, and the residue was purified by silica gel column chromatography (developing solvent: hexane/ethyl acetate) to obtain the entitled compound.

(Step 3)

Synthesis of 4-[(2-(difluoromethoxy)pyridin-3-yl]oxy)-3-fluoroaniline

A developed Raney nickel catalyst was added to a methanol (25 ml) solution of the nitro compound (3.6 g) obtained in the step 2, and stirred in a hydrogen atmosphere at room temperature for 4 hours. After purging with nitrogen, the insoluble matter was removed by filtration, and the filtrate was concentrated. The residue was purified by silica gel column chromatography (developing solvent: hexane/ethyl acetate) to obtain the entitled compound.

(Step 4)

Synthesis of 4-([2-(difluoromethoxy)pyridin-3-yl]oxy)-5-fluoro-2-nitroaniline

Potassium nitrate (1.0 g) was added to a trifluoroacetic acid solution of the aniline compound (2.5 g) obtained in the step 3, and stirred overnight at room temperature. The solvent was evaporated away under reduced pressure, the residue was neutralized with aqueous saturated sodium hydrogencarbonate solution, and extracted with ethyl acetate. After dried, the solvent was evaporated away under reduced pressure, the residue was purified by silica gel column chromatography (developing solvent: hexane/ethyl acetate), and the obtained crude crystal was washed with chloroform/hexane to obtain the entitled compound as a yellow solid.

(Step 5)

Synthesis of 2-(difluoromethoxy)-3-(2-([6-(ethylsulfonyl)pyridin-3-yl]oxy)-4-iodo-5-nitrophenoxy)pyridine A water (4 ml) solution of sodium nitrite (96 mg) and 4 N hydrochloric acid/dioxane solution (960 µl) were added to a 1,4-dioxane (4 ml) solution of the nitroaniline compound (400 mg) obtained in the step 4, and stirred for 1 hour with cooling with ice. A water (4 ml) solution of potassium iodide (256 mg) was added, then stirred for 2 hours with gradually heating up to room temperature. Aqueous 10% sodium hydrogensulfite solution was added, then extracted with ethyl acetate, and the organic layer was washed with saturated saline water. After dried, the solvent was evaporated away under reduced pressure, and the residue was purified by silica gel column chromatography (developing solvent: hexane/ethyl acetate).

6-(Ethylsulfonyl)-3-pyridinol (160 mg) obtained in Reference Example 3 and potassium carbonate (208 mg) were added to an N,N-dimethylformamide (4 ml) solution of the obtained compound, and stirred overnight at 100° C. With cooling with ice, water was added, then extracted with ethyl acetate, and the organic layer was washed with saturated saline water. After dried, the solvent was evaporated away under reduced pressure, and the residue was purified by silica gel column chromatography (developing solvent: hexane/ethyl acetate) to obtain the entitled compound.

(Step 6)

Synthesis of 2-(difluoromethoxy)-3-[2-([6-(ethylsulfonyl)pyridin-3-yl]oxy)-5-nitro-4-(pyridin-2-ylethynyl)phenoxy]pyridine Bis(triphenylphosphine)palladium(II) dichloride complex (11 mg) and copper(I) iodide (13 mg) were added to an N,N-dimethylformamide (1 ml)/triethylamine (2 ml) mixed solution of the iodobenzene compound (85 mg) obtained in the step 5, and with cooling with ice, 2-ethynylpyridine (16 mg) was added, and stirred at room temperature for 2 hours. With cooling with ice, water was added, diluted with ethyl acetate, and the insoluble matter was removed through filtration. The filtrate was washed with aqueous saturated ammonium chloride solution and saturated saline water. After dried, the solvent was evaporated away under reduced pressure, and the residue was purified by silica gel column chromatography (developing solvent: chloroform/methanol) to obtain the entitled compound.

(Step 7)

Synthesis of 5-([2-(difluoromethoxy)pyridin-3-yl]oxy)-4-([6-(ethylsulfonyl)pyridin-3-yl]oxy)-2-(pyridin-2-ylethynyl)aniline Stannous(II) chloride dihydrate (40 mg) was added to an ethanol (1 ml) solution of the nitrobenzene compound (46 mg) obtained in the step 6, and stirred at 50° C. for 30 minutes. Further, N,N-dimethylformamide (1 ml) was added, and stirred at 50° C. for 30 minutes. With cooling with ice, aqueous saturated sodium hydrogencarbonate solution and ethyl acetate were added, stirred at room temperature for 30 minutes, and the insoluble matter was removed by filtration. The filtrate was washed with water and saturated saline water. After dried, the solvent was evaporated away under reduced pressure, and the residue was purified by partitioning thin-layer chromatography (Kieselgel™ 60F254, Art 5744, by Merck, chloroform/methanol=15/1) to obtain the entitled compound.

(Step 8)

Synthesis of 6-([2-(difluoromethoxy)pyridin-3-yl]oxy)-5-([6-(ethylsulfonyl)pyridin-3-yl]oxy)-2-pyridin-2-yl-1H-indole Potassium t-butoxide was added to an N-methyl-2-pyrrolidinone (2.1 ml) solution of the acetylene compound (12 mg) obtained in the step 7, and stirred at room temperature. Potassium t-butoxide was suitably added until disappearance of the acetylene compound. With cooling with ice, aqueous saturated ammonium chloride solution was added, then extracted with ethyl acetate, and the organic layer was washed with saturated saline water. After dried, the solvent was evaporated away under reduced pressure, and the residue was purified by partitioning reversed-phase chromatography to obtain the entitled compound.

1H-NMR (CDCl$_3$) δ: 1.28 (3H, t, J=7.6 Hz), 3.34 (2H, q, J=7.6 Hz), 7.01 (1H, d, J=1.2 Hz), 7.03 (1H, dd, J=8.6, 4.7 Hz), 7.11 (1H, s), 7.19-7.28 (3H, m), 7.36 (1H, t, J=72.8 Hz), 7.50 (1H, s), 7.72-7.80 (2H, m), 7.89 (1H, dd, J=4.5, 1.8 Hz), 7.96 (1H, d, J=8.6 Hz), 8.36 (1H, d, J=2.7 Hz), 8.57 (1H, d, J=4.5 Hz), 9.71 (1H, brs).

ESI-MASS (m/e): 539[M+H]

Example 3

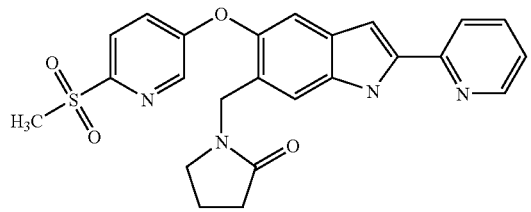

1-[(5-([6-(Methylsulfonyl)pyridin-3-yl]oxy)-2-pyridin-2-yl-1H-indol-6-yl)methyl]p-pyrrolidin-2-one (Step 1)

Synthesis of 2-([6-(methylsulfonyl)pyridin-3-yl]oxy)-5-nitrobenzaldehyde

Cesium carbonate (10 g) was added to an N-methylpyrrolidinone (70 ml) solution of 2-chloro-5-nitrobenzaldehyde (5.0 g) and 6-(methylsulfonyl)-3-pyridinol (5 g) obtained in Reference Example 2, and stirred at room temperature for 3 hours. Water was added, then the formed crystal was collected by filtration to obtain the entitled compound as a pale brown solid.

(Step 2)

Synthesis of methyl 4-[(2-([6-(methylsulfonyl)pyridin-3-yl]oxy)-5-nitrobenzyl)amino]butyrate A methanol solution (5 ml) of 0.25 M sodium cyanoborate-½ zinc chloride complex was added to a methanol (2 ml) suspension of the aldehyde compound (200 mg) obtained in the step 1 and methyl 4-aminobutyrate hydrochloride (115 mg), and stirred at room temperature for 30 minutes. Aqueous saturated sodium hydrogencarbonate solution and saturated saline water were added, then extracted with ethyl acetate, and the organic layer was washed with water and saturated saline water. After dried, the solvent was evaporated away under reduced pressure to obtain the entitled compound as a brown amorphous substance.

(Step 3)

Synthesis of 1-(2-([6-(methylsulfonyl)pyridin-3-yl]oxy)-5-nitrobenzyl)pyrrolidin-2-one 25% sodium methoxide/methanol solution (30 µl) was added to a methanol (4 ml) solution of the ester compound (219 mg) obtained in the step 2, and stirred overnight at room temperature. After concentrated, the residue was purified by silica gel column chromatography (developing solvent: chloroform/methanol) to obtain the entitled compound as a pale yellow oil.

(Step 4)

Synthesis of 1-(5-amino-2-([6-(methylsulfonyl)pyridin-3-yl]oxy)benzyl)pyrrolidin-2-one A developed Raney nickel catalyst was added to a methanol solution of the nitro compound (120 mg) obtained in the step 3, and stirred in a hydrogen atmosphere for 1 hour. After purging with nitrogen, the insoluble matter was removed by filtration, and the filtrate was concentrated. A developed Raney nickel catalyst and hydrazine hydrate (70 µl) were added to a methanol solution of the obtained compound, and stirred for 1 hour. The insoluble matter was removed by filtration, and the filtrate was concentrated to obtain the entitled compound as a yellow solid.

(Step 5)

Synthesis of 1-(5-amino-4-iodo-2-([6-(methylsulfonyl)pyridin-3-yl]oxy)benzyl)pyrrolidin-2-one Silver nitrate (935 mg) was added to a chloroform (10 ml)/ethanol (10 ml) mixed solution of the aniline compound (834 mg) obtained in the step 4, and with cooling with ice, iodine (645 mg) was added. After shielded from light, this was stirred overnight under a nitrogen atmosphere at room temperature. After diluted with chloroform, an aqueous sodium sulfite solution was added and stirred for 1 hour with cooling with ice. The insoluble matter was removed by filtration, the filtrate was extracted with chloroform, and the organic layer was washed with saturated saline water. After dried, the solvent was evaporated away under reduced pressure, and the residue was purified by silica gel column chromatography (developing solvent: chloroform/methanol) to obtain the entitled compound.

(Step 6)

Synthesis of ethyl (2-iodo-4-([6-(methylsulfonyl)pyridin-3-yl]oxy)-5-[(2-oxopyrrolidin-1-yl)methyl]phenyl)carbamate Ethyl chloroformate was added to a pyridine (20 ml) solution of the aniline compound (754 mg) obtained in the step 5, and stirred overnight at room temperature. The solvent was concentrated, diluted with chloroform, and washed with aqueous saturated ammonium chloride solution and saturated saline water. After dried, the solvent was evaporated away under reduced pressure, and the residue was purified by silica gel column chromatography (developing solvent: chloroform/methanol) to obtain the entitled compound.

(Step 7)

Synthesis of ethyl [4-([6-(methylsulfonyl)pyridin-3-yl]oxy)-5-[(2-oxopyrrolidin-1-yl)methyl]-2-(pyridin-2-ylethynyl)phenyl]carbamate Bis(triphenylphosphine)palladium(II) dichloride complex (6.3 mg) and copper(I) iodide (3.4 mg) were added to a dimethylformamide (1 ml)/triethylamine (1 ml) mixed solution of the aryl iodide compound (48 mg) obtained in the step 6, and then with cooling with ice, 2-ethynylpyridine (10.5 mg) wad added, and stirred overnight at room temperature. Water was added with cooling with ice, then extracted with ethyl acetate, and the insoluble matter was removed by filtration. The filtrate was washed with water, aqueous saturated ammonium chloride solution and saturated saline water. After dried, the solvent was evaporated away under reduced pressure, and the residue was purified by silica gel column chromatography (developing solvent: chloroform/methanol) and partitioning thin-layer chromatography (Kieselgel™ 60F254, Art 5744, by Merck, chloroform/methanol 10/1) to obtain the entitled compound.

(Step 8)

Synthesis of 1-[(5-([6-(methylsulfonyl)pyridin-3-yl]oxy)-2-pyridin-2-yl-1H-indol-6-yl)methyl]pyrrolidin-2-one 1.0 M tetra(n-butyl)ammonium fluoride/tetrahydrofuran solution (20 μl) was added to a tetrahydrofuran (1 ml) solution of the acetylene compound (27 mg) obtained in the step 7, and stirred overnight at 50° C. With cooling with ice, water was added, then extracted with chloroform, and the organic layer was washed with 1.0 M phosphate buffer (pH 6.8) and saturated saline water. After dried, the solvent was evaporated away under reduced pressure, and the residue was purified by partitioning thin-layer chromatography (Kieselgel™ 60F254, Art 5744, by Merck, chloroform/methanol=10/1) to obtain the entitled compound as a white amorphous substance.

1H-NMR (CDCl₃) δ: 1.90-1.96 (2H, m), 2.29-2.34 (2H, m), 3.22 (3H, s), 3.27-3.31 (2H, m), 4.50 (2H, s), 6.97 (1H, d, J=1.2 Hz), 7.21-7.25 (1H, m), 7.31 (1H, s), 7.32 (2H, dd, J=8.6, 2.7 Hz), 7.45 (1H, s), 7.73-7.82 (2H, m), 8.00 (1H, d, J=8.6 Hz), 8.44 (1H, d, J=2.7 Hz), 8.61 (1H, d, J=4.3 Hz), 9.64 (1H, brs).

ESI-MASS (m/e): 463[M+H]

Example 4

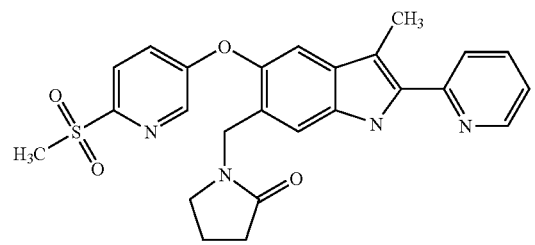

1-[(3-Methyl-5-([6-(methylsulfonyl)pyridin-3-yl]oxy)-2-pyridin-2-yl-1H-indol-6-yl)methyl]pyrrolidin-2-one (Step 1)

Synthesis of 1-[(5-([6-(methylsulfonyl)pyridin-3-yl]oxy)-2-pyridin-2-yl-1-([2-(trimethylsilyl)ethoxy]methyl)-1H-indol-6-yl)methyl]pyrrolidin-2-one With cooling with ice, sodium hydride (30% liquid paraffin added) (6 mg) was added to an N,N-dimethylformamide (2 ml) solution of the indole compound (50 mg) obtained in Example 3, then 2-(trimethylsilyl)ethoxy methyl chloride (24 mg) was added, and stirred at room temperature for 1 hour. With cooling with ice, aqueous saturated ammonium chloride solution was added, then extracted with ethyl acetate, and the organic layer was washed with water and saturated saline water. After dried, the solvent was evaporated away under reduced pressure, and the residue was purified by partitioning reversed-phase liquid chromatography to obtain the entitled compound.

(Step 2)

Synthesis of 1-[(3-bromo-5-([6-(methylsulfonyl)pyridin-3-yl]oxy)-2-pyridin-2-yl-1-([2-(trimethylsilyl)ethoxy]methyl)-1H-indol-6-yl)methyl]pyrrolidin-2-one With cooling with ice, N-bromosuccinimide (5.7 mg) was added to a dichloromethane (500 μl) solution of the indol compound (17 mg) obtained in the step 1, and stirred for 20 minutes. This was diluted with ethyl acetate, then washed with aqueous saturated sodium hydrogencarbonate solution and saturated saline water. After dried, the solvent was evaporated away under reduced pressure, and the residue was purified by partitioning thin-layer chromatography (Kieselgel™ 60F254, Art 5744, by Merck, chloroform/methanol=10/1) to obtain the entitled compound.

(Step 3)

Synthesis of 1-[(3-methyl-5-([6-(methylsulfonyl)pyridin-3-yl]oxy)-2-pyridin-2-yl-1-([2-(trimethylsilyl)ethoxy]methyl)-1H-indol-6-yl)methyl]pyrrolidin-2-one 1.0 M dimethylzinc/hexane solution (30 µl) and bis(triphenylphosphine)palladium(II) dichloride complex (2 mg) were added to a tetrahydrofuran solution of the bromine compound (15 mg) obtained in the step 2, then 2-dimethylaminoethanol (10 µl) was added and stirred under a nitrogen atmosphere at 70° C. for 30 minutes. Aqueous saturated sodium hydrogencarbonate solution was added, then extracted with ethyl acetate, and the organic layer was washed with saturated saline water. After dried, the solvent was evaporated away under reduced pressure, and the residue was purified by partitioning reversed-phase liquid chromatography to obtain the entitled compound.

(Step 4)

Synthesis of 1-[(3-methyl-5-([6-(methylsulfonyl)pyridin-3-yl]oxy)-2-pyridin-2-yl-1H-indol-6-yl)methyl]pyrrolidin-2-one The methylindole compound (7.3 mg) obtained in the step 3 was dissolved in trifluoroacetic acid (500 µl) and water (100 µl), and stirred at room temperature for 30 minutes. This was further stirred at 80° C. for 30 minutes. The solvent was evaporated away, the residue was neutralized with triethylamine and purified by partitioning thin-layer chromatography (Kieselgel™ 60F254, Art 5744, by Merck, chloroform/methanol=10/1) to obtain the entitled compound as a white solid.

$^1$H-NMR (CDCl$_3$) δ: 1.88-1.95 (2H, m), 2.30 (2H, t, J=8.2 Hz), 2.56 (3H, s), 3.22 (3H, s), 3.27 (2H, t, J=7.0 Hz), 4.50 (2H, s), 7.21-7.25 (1H, m), 7.28 (1H, s), 7.31 (1H, dd, J=8.6, 2.7 Hz), 7.40 (1H, s), 7.78-7.81 (2H, m), 8.00 (1H, d, J=8.6 Hz), 8.43 (1H, d, J=2.7 Hz), 8.65 (1H, d, J=5.1 Hz), 9.58 (1H, brs).

ESI-MASS (m/e): 477[M+H]

Example 5

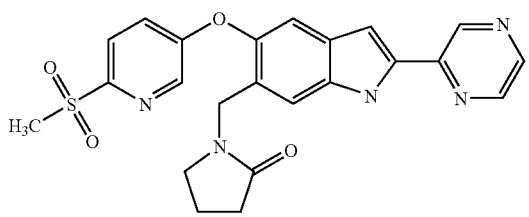

1-[(5-([6-(Methylsulfonyl)pyrazin-3-yl]oxy)-2-pyridin-2-yl-1H-indol-6-yl)methyl]pyrrolidin-2-one Using 2-ethynylpyrazine obtained in Reference Example 5, and according to the same method as in Example 3 or according to a method similar to it or according to a combination of the method with an ordinary method, the entitled compound was obtained.

$^1$H-NMR (CDCl$_3$) δ: 1.91-1.99 (2H, m), 2.34 (2H, t, J=8.0 Hz), 3.22 (3H, s), 3.31 (2H, t, J=7.1 Hz), 4.51 (2H, s), 7.11 (1H, s), 7.31-7.34 (1H, m), 7.34 (1H, s), 7.49 (1H, s), 8.01 (1H, dd, J=8.6, 0.6 Hz), 8.44 (1H, d, J=2.7 Hz), 8.48 (1H, d, J=2.7 Hz), 8.54-8.56 (1H, m), 9.09 (1H, s), 9.58 (1H, brs).

ESI-MASS (m/e): 464[M+H]

Example 6

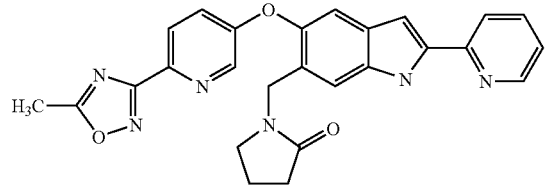

1-[(5-([6-(5-Methyl-1,2,4-oxadiazol-3-yl)pyridin-3-yl]oxy)-2-pyridin-2-yl-1H-indol-6-yl)methyl]pyrrolidin-2-one Using 6-(5-methyl-1,2,4-oxadiazol-3-yl)-3-pyridinol obtained in Reference Example 4, and according to the same method as in Example 3 or according to a method similar to it or according to a combination of the method with an ordinary method, the entitled compound was obtained.

$^1$H-NMR (CDCl$_3$) δ: 1.88-1.95 (2H, m), 2.32 (2H, t, J=8.1 Hz), 2.68 (3H, s), 3.30 (2H, t, J=7.0 Hz), 4.55 (2H, s), 6.96 (1H, d, J=2.0 Hz), 7.21 (1H, dd, J=6.9, 5.3 Hz), 7.29 (1H, dd, J=8.6, 2.7 Hz), 7.30 (1H, s), 7.45 (1H, s), 7.71-7.81 (2H, m), 8.02 (1H, d, J=8.6 Hz), 8.52 (1H, d, J=2.7 Hz), 8.60 (1H, d, J=5.3 Hz), 9.69 (1H, brs).

ESI-MASS (m/e): 467[M+H]

Example 7

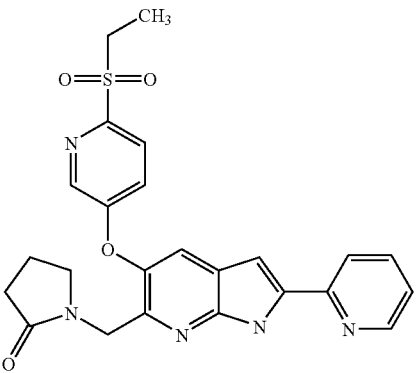

1-[(5-([6-(Ethylsulfonyl)pyridin-3-yl]oxy)-2-pyridin-2-yl-1H-pyrrolo[2,3-b]pyridin-6-yl)methyl]pyrrolidin-2-one (Step 1)

Synthesis of 2-bromo-6-methylpyridin-3-ol

With cooling with ice, N-bromosuccinimide (18 g) was added to a pyridine (75 ml) solution of 6-methylpyridin-3-ol (10 g), and stirred at room temperature for 4 hours. After further stirred overnight at 50° C., the solvent was evaporated away under reduced pressure. The residue was dissolved in ethyl acetate, and washed with aqueous saturated sodium hydrogencarbonate solution and saturated saline water. After dried, the solvent was evaporated away, and the residue was crystallized with chloroform to obtain the entitled compound as a white solid.

(Step 2)

Synthesis of 2-bromo-3-([6-(ethylsulfonyl)pyridin-3-yl]oxy)-6-methylpyridin

Cesium carbonate was added to an N-methylpyrrolidinone (30 ml) solution of the phenol compound (2 g) obtained in the step 1 and 3-chloro-6-(ethylsulfonyl)pyridine (2.2 g), and stirred at 100° C. for 5 hours. This was further stirred overnight at 115° C., then diluted with ethyl acetate, and washed with water and saturated saline water. After dried, the solvent was evaporated away under reduced pressure, and the residue was purified by silica gel column chromatography (developing solvent: hexane/ethyl acetate) to obtain the entitled compound.

(Step 3)

Synthesis of 6-bromo-5-([6-(ethylsulfonyl)pyridin-3-yl]oxy)pyridine-2-carboxylic acid An aqueous solution (5.2 ml) of 0.05 M dichloro(bipyridyl)nickel complex prepared according to the method described in SYNTHETIC COMMUNICATIONS, 1999, Vol. 29, No. 13, p. 2211 was added to an acetonitrile (13 ml) solution of the methylpyridine compound (920 mg) obtained in the step 2, and stirred overnight at room temperature. Aqueous sodium hydrogensulfite solution was added, then extracted with ethyl acetate, and the organic layer was washed with water and saturated saline water. After dried, the solvent was evaporated away under reduced pressure to obtain the entitled compound as a colorless oil.

(Step 4)

Synthesis of 6-bromo-5-([6-(ethylsulfonyl)pyridin-3-yl]oxy)pyridine-2-amine

Triethylamine (450 μl) and diphenylphosphoryl azide (650 μl) were added to a toluene (10 ml)/t-butanol (10 ml) mixed solution of the carboxylic acid (735 mg) obtained in the step 3, and stirred overnight at 100° C. The solvent was evaporated away under reduced pressure, and the residue was purified by silica gel column chromatography (developing solvent: hexane/ethyl acetate) to obtain a white solid (222 mg).

The obtained white solid (165 mg) was dissolved in 4 N hydrochloric acid/dioxane solution, and stirred at room temperature. After concentrated, this was diluted with ethyl acetate, and washed with water and aqueous saturated sodium hydrogencarbonate solution. After dried, the solvent was evaporated away to obtain the entitled compound as a pale yellow solid.

(Step 5)

Synthesis of 6-bromo-5-([6-(ethylsulfonyl)pyridin-3-yl]oxy)-3-iodopyridine-2-amine Silver sulfate (170 mg) was added to a chloroform (4 ml)/ethanol (4 ml) mixed solution of the aminopyridine compound (150 mg) obtained in the step 4, and with cooling with ice, iodine (117 mg) was added. After shielded from light, this was stirred overnight under a nitrogen atmosphere at room temperature. This was diluted with chloroform, then with cooling with ice, an aqueous sodium sulfite solution was added and stirred for 1 hour. The insoluble matter was removed by filtration, the filtrate was extracted with chloroform, and the organic layer was washed with saturated saline water. After dried, the solvent was evaporated away under reduced pressure, and the residue was purified by silica gel column chromatography (developing solvent: chloroform/methanol) to obtain the entitled compound.

(Step 6)

Synthesis of 6-bromo-5-([6-(ethylsulfonyl)pyridin-3-yl]oxy)-3-(pyridin-2-ylethynyl)pyridine-2-amine Bis(triphenylphosphine)palladium(II) dichloride complex (23 mg) and copper(I) iodide (13 mg) were added to a dimethylformamide (2 ml)/triethylamine (2 ml) mixed solution of the iodopyridine compound (161 mg) obtained in the step 5, then with cooling with ice, 2-ethynylpyridine (41 mg) was added, and stirred under a nitrogen atmosphere at room temperature for 2 hours. With cooling with ice, water was added, then diluted with chloroform, and the insoluble matter was removed by filtration. The filtrate was washed with aqueous saturated ammonium chloride solution and saturated saline water. After dried, the solvent was evaporated away under reduced pressure, and the residue was purified by silica gel column chromatography (developing solvent: chloroform/methanol) to obtain the entitled compound.

(Step 7)

Synthesis of N-[6-bromo-5-([6-(ethylsulfonyl)pyridin-3-yl]oxy)-3-(pyridin-2-ylethynyl)pyridin-2-yl]-2,2,2-trifluoroacetamide Trifluoroacetic anhydride (188 mg) was added to a tetrahydrofuran (6 ml) solution of the aminopyridine compound (137 mg) obtained in the step 6, and stirred at room temperature for 6 hours. This was diluted with ethyl acetate, and washed with aqueous saturated sodium hydrogencarbonate solution and saturated saline water. After dried, the solvent was evaporated away, and the residue was purified by silica gel column chromatography (developing solvent: chloroform/methanol) to obtain the entitled compound.

(Step 8)

Synthesis of 6-bromo-5-([6-(ethylsulfonyl)pyridin-3-yl]oxy)-2-pyridin-2-yl-1H-pyrrolo[2,3-b]pyridine Potassium tert-butoxide (60 mg) was added to an N-methyl-2-pyrrolidinone (2.5 ml) solution of the acetylene compound (148 mg) obtained in the step 7, and then stirred at 120° C. for 7 hours. This was diluted with ethyl acetate, and with cooling with ice, aqueous saturated ammonium chloride solution was added. The organic layer was washed with water and saturated saline water. After dried, the solvent was evaporated away under reduced pressure, and the residue was purified by silica gel column chromatography (developing solvent: chloroform/methanol) to obtain the entitled compound as a yellow amorphous substance.

(Step 9)

Synthesis of 6-bromo-5-([6-(ethylsulfonyl)pyridin-3-yl]oxy)-2-pyridin-2-yl-1-([2-(trimethylsilyl)ethoxy]methyl)-1H-pyrrolo[2,3-b]pyridine With cooling with ice, sodium hydride (30% liquid paraffin added) (10 mg) was added to an N,N-dimethylformamide (2 ml) solution of the pyrrolo[2,3-b]pyridine compound (83 mg) obtained in the step 8, then 2-(trimethylsilyl)ethoxymethyl chloride (36 mg) was added and stirred at room temperature for 30 minutes. With cooling with ice, aqueous saturated ammonium chloride solution was added, then extracted with ethyl acetate, and the organic layer was washed with water and saturated saline water. After dried, the solvent was evaporated away under reduced pressure, and the residue was purified by silica gel column chromatography (developing solvent: hexane/ethyl acetate) to obtain the entitled compound as a yellow oil.

(Step 10)

Synthesis of 5-([6-(ethylsulfonyl)pyridin-3-yl]oxy)-2-pyridin-2-yl-1-([2-(trimethylsilyl)ethoxy]methyl)-6-vinyl-1H-pyrrolo[2,3-b]pyridine Tri(n-butyl)vinyltin (43 mg) and tetrakis(triphenylphosphine)palladium(0) complex (14 mg) were added to a toluene (1 ml) solution of the pyrrolo[2,3-b]pyridine compound (67 mg) obtained in the step 9, and heated under reflux under a nitrogen atmosphere for 4 hours. Saturated saline water was added, and then extracted with ethyl acetate. After dried, the solvent was evaporated away under reduced pressure, and the residue was purified by silica gel column chromatography (developing solvent: hexane/ethyl acetate) to obtain the entitled compound as a yellow oil.

(Step 11)

Synthesis of 1-[5-([6-(ethylsulfonyl)pyridin-3-yl]oxy)-2-pyridin-2-yl-1-([2-(trimethylsilyl)ethoxy]methyl)-1H-pyrrolo[2,3-b]pyridin-6-yl)methyl]pyrrolidin-2-one 0.1 M osmium tetroxide/water solution (77 μl) and sodium periodate (49 mg) were added to a tetrahydrofuran (1 ml) solution of the vinyl compound (41 mg) obtained in the step 10, and stirred at room temperature for 5 hours. This was diluted with ethyl acetate, then 10% sodium sulfite/water solution was added, and stirred at room temperature for 1 hour. After extracted with ethyl acetate, the organic layer was washed with aqueous saturated sodium hydrogencarbonate solution and saturated saline water. After dried, the solvent was evaporated away under reduced pressure to obtain a crude product (40 mg) as a yellow oil.

Triethylamine (22 μl) and methyl 4-aminobutyrate hydrochloride (26 mg) were added to a chloroform (1 ml) solution of the obtained yellow oil (40 mg), then sodium triacetoxyborohydride (33 mg) was added, and stirred overnight at room temperature. With cooling with ice, aqueous saturated sodium hydrogencarbonate solution was added, then extracted with chloroform, and the organic layer was washed with saturated saline water. After dried, the solvent was evaporated away under reduced pressure, and the residue was purified by partitioning thin-layer chromatography Kieselgel™ 60F254, Art 5744, by Merck, chloroform/methanol=15/1) to obtain the entitled compound as a pale yellow amorphous substance.

(Step 12)

Synthesis of 1-[(5-([6-(ethylsulfonyl)pyridin-3-yl]oxy)-2-pyridin-2-yl-1H-pyrrolo[2,3-b]pyridin-6-yl)methyl]pyrrolidin-2-one The pyrrolo[2,3-b]pyridine compound (25 mg) obtained in the step 11 was dissolved in trifluoroacetic acid (600 μl) and water (100 μl), and stirred at 80° C. for 30 minutes. The solvent was evaporated away, then diluted with chloroform with cooling with ice, and neutralized with aqueous saturated sodium hydrogencarbonate solution. This was extracted with chloroform and washed with saturated saline water. After dried, the solvent was evaporated away under reduced pressure, and the residue was purified by partitioning thin-layer chromatography (Kieselgel™ 60F254, Art 5744, by Merck, chloroform/methanol=10/1) to obtain the entitled compound as a pale yellow crystal.

$^1$H-NMR (CDCl$_3$) δ: 1.32 (3H, t, J=7.4 Hz), 1.91-1.99 (2H, m), 2.30 (2H, t, J=8.1 Hz), 3.36-3.43 (2H, m), 3.40 (2H, q, J=7.4 Hz), 4.66 (2H, s), 6.93 (1H, d, J=2.0 Hz), 7.24-7.29 (1H, m), 7.35 (1H, dd, J=8.6, 2.7 Hz), 7.63 (1H, s), 7.75-7.84 (2H, m), 8.03 (1H, d, J=8.6 Hz), 8.46 (1H, d, J=2.7 Hz), 8.65 (1H, d, J=4.9 Hz), 9.98 (1H, brs).

ESI-MASS (m/e): 478[M+H]

Example 8

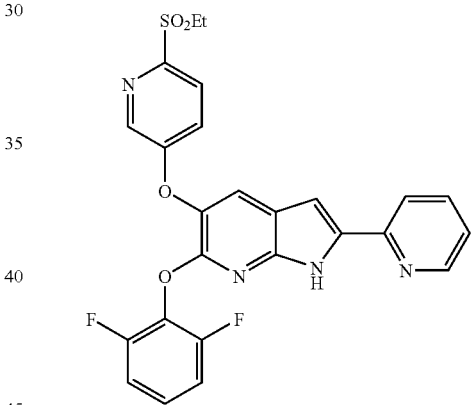

6-(2,6-Difluorophenoxy)-5-{[6-(ethylsulfonyl)pyridin-3-yl]oxy}-2-pyridin-2-yl-1H-pyrrolo[2,3-b]pyridine (Step 1)

Synthesis of 2-chloro-3-{[6-(ethylsulfonyl)pyridin-3-yl]oxy}pyridine

Cesium carbonate (20 g) was added to an N-methyl-2-pyrrolidinone (160 ml) solution of 2-chloro-3-hydroxypyridine (6 g) and 5-chloro-2-(ethylsulfonyl)pyridine (4.8 g), and stirred at 100° C. for 24 hours. After this was diluted with ethyl acetate, aqueous saturated ammonium chloride solution was added with cooling with ice. The organic layer was washed with water and saturated saline water. After dried, the solvent was evaporated away under reduced pressure, and the residue was purified by silica gel column chromatography (developing solvent: hexane/ethyl acetate) to obtain the entitled compound as a brown oil.

(Step 2)

Synthesis of 2-chloro-3-{[6-(ethylsulfonyl)pyridin-3-yl]oxy}pyridin N-oxide

Urea hydrogen peroxide (4.7 g) was added to a dichloromethane (70 ml) solution of the pyridine compound (7.1 g) obtained in the step 1, then trifluoroacetic anhydride (6.7 ml) was added dropwise, and stirred at room temperature for 20 minutes. With cooling with ice, aqueous 10% sodium thiosulfate solution was added, and stirred at room temperature for 30 minutes. The reaction solution was extracted with chloroform, then the organic layer was washed with aqueous saturated sodium hydrogencarbonate solution and saturated saline water. After dried, the solvent was evaporated away under reduced pressure, and the residue was purified by silica gel column chromatography (developing solvent: chloroform/methanol) to obtain the entitled compound as a white solid.

(Step 3)

Synthesis of 6-chloro-5-{[6-(ethylsulfonyl)pyridin-3-yl]oxy}pyridine-2-carbonitrile With cooling with ice, triethylamine (2.7 ml) and dimethylcarbamyl chloride (1.8 ml) were added to an acetonitrile (70 ml) solution of the pyridine N-oxide compound (3 g) obtained in the step 2, and stirred at room temperature for 1 hour. Trimethylsilylcyanide (3.8 ml) was added to the reaction solution, and stirred overnight at 80° C. With cooling with ice, aqueous saturated sodium hydrogencarbonate solution was added, then extracted with chloroform, and the organic layer was washed with saturated saline water. After dried, the solvent was evaporated away under reduced pressure, and the residue was purified by silica gel column chromatography (developing solvent: hexane/ethyl acetate) to obtain the entitled compound.

(Step 4)

Synthesis of 6-(2,6-difluorophenoxy)-5-{[6-(ethylsulfonyl)pyridin-3-yl]oxy}pyridine-2-carbonitrile Potassium carbonate (920 mg) was added to an N,N-dimethylformamide (33 ml) solution of the chloropyridine-carbonitrile compound (1 g) obtained in the step 3 and 2,6-difluorophenol (480 mg), and stirred at 80° C. for 1 hour. With cooling with ice, aqueous saturated ammonium chloride solution was added, then extracted with chloroform, and the organic layer was washed with water and saturated saline water. After dried, the solvent was evaporated away under reduced pressure, and the residue was purified by silica gel column chromatography (developing solvent: hexane/ethyl acetate) to obtain the entitled compound as a yellow white solid.

(Step 5)

Synthesis of 6-(2,6-difluorophenoxy)-5-{[6-(ethylsulfonyl)pyridin-3-yl]oxy}pyridine-2-carboxylic acid A 10% hydrochloric acid/methanol solution of the pyridine-carbonitrile compound (490 mg) obtained in the step 4 was stirred overnight at 80° C. After concentrated, the residue was dissolved in a tetrahydrofuran (10 ml)/methanol (10 ml) mixed solution, then aqueous 5 N sodium hydroxide solution (5 ml) was added, and stirred at room temperature for 1 hour. The reaction mixture was neutralized with 10% citric acid solution, then extracted with chloroform, and the organic layer was washed with water and saturated saline water. After dried, the solvent was evaporated away under reduced pressure to obtain the entitled compound as a white amorphous substance.

(Step 6)

Synthesis of 6-(2,6-difluorophenoxy)-5-{[6-(ethylsulfonyl)pyridin-3-yl]oxy}pyridine-2-amine Triethylamine (300 µl) and diphenylphosphorylazide (547 µl) were added to a t-butyl alcohol (5 ml)/toluene (5 ml) mixed solution of the carboxylic acid (465 mg) obtained in the step 5, and stirred at 80° C. for 4 hours. With cooling with ice, saturated saline water was added, and extracted with chloroform. After dried, the solvent was evaporated away under reduced pressure, and the obtained residue was dissolved in 4 N hydrochloric acid/dioxane solution (10 ml), and stirred overnight at room temperature. After concentrated, this was diluted with chloroform, and neutralized with aqueous saturated sodium hydrogencarbonate solution. After extracted with chloroform, the organic layer was washed with saturated saline water. After dried, the organic solvent was evaporated away under reduced pressure, and the residue was purified by silica gel column chromatography (developing solvent: hexane/ethyl acetate) to obtain the entitled compound as a white amorphous substance.

(Step 7)

Synthesis of 6-(2,6-difluorophenoxy)-5-{[6-(ethylsulfonyl)pyridin-3-yl]oxy}-3-iodopyridine-2-amine Using the aminopyridine compound obtained in the step 6 and in the same manner as in the step 5 of Example 7, or according to a method similar to it, or according to a combination of the method with an ordinary method, the entitled compound was obtained.

(Step 8)

Synthesis of 6-(2,6-difluorophenoxy)-5-{[6-(ethylsulfonyl)pyridin-3-yl]oxy}-3-(pyridin-2-ylethynyl)pyridine-2-amine Using the iodopyridine compound obtained in the step 7 and in the same manner as in the step 6 of Example 7, or according to a method similar to it, or according to a combination of the method with an ordinary method, the entitled compound was obtained.

(Step 9)

Synthesis of N-[6-(2,6-difluorophenoxy)-5-{[6-(ethylsulfonyl)pyridin-3-yl]oxy}-3-(pyridin-2-ylethynyl)pyridin-2-yl]-2,2,2-trifluoroacetamide Using the aminopyridine compound obtained in the step 8 and in the same manner as in the step 7 of Example 7, or according to a method similar to it, or according to a combination of the method with an ordinary method, the entitled compound was obtained.

(Step 10)

Synthesis of 6-(2,6-difluorophenoxy)-5-{[6-(ethylsulfonyl)pyridin-3-yl]oxy}-2-pyridin-2-yl-1H-pyrrolo[2,3-b]pyridine Using the acetylene compound obtained in the step 9 and in the same manner as in the step 8 of Example 7, or according to a method similar to it, or according to a combination of the method with an ordinary method, the entitled compound was obtained as a white solid.

$^1$H-NMR (CDCl$_3$) δ: 1.30 (t, 3H, J=7.5 Hz), 3.39 (q, 2H, J=7.5 Hz), 6.93 (d, 1H, J=2.2 Hz), 6.96-7.04 (m, 2H), 7.15-7.23 (m, 2H), 7.39 (dd, 1H, J=8.6, 2.7 Hz), 7.69-7.77 (m, 2H), 7.83 (s, 1H), 8.04 (d, 1H, J=8.6 Hz), 8.52-8.55 (m, 1H), 8.60 (d, 1H, J=2.7 Hz), 9.77 (brs, 1H).

ESI-MASS (m/e): 509[M+H]

Reference Example 1

Synthesis of 4-(methylsulfonyl)phenol

In a water bath, methyl iodide (18.5 ml) and potassium carbonate (28.7 g) were added to an acetone (250 ml) solution of 4-hydroxythiophenol (25 g), and stirred at room temperature for 5 hours. The salt was removed by filtration, the solvent was evaporated away under reduced pressure, diethyl ether was added, and extracted with aqueous 2 N sodium hydroxide solution. The obtained aqueous layer was made acidic with aqueous 6 N hydrochloric acid solution, extracted with diethyl ether, and the organic layer was washed with aqueous saturated sodium chloride solution. After dried, the solvent was evaporated away under reduced pressure to obtain 4-(methylsulfanyl)phenol (27.3 g) as a pale yellow solid. In a water bath, 30% hydrogen peroxide water (67 ml) was gradually and added dropwise to an acetic acid (130 ml) solution of 4-(methylsulfanyl)phenol (27.3 g). After the addition, this was gradually heated up to 100° C., and stirred for 1 hour. The reaction solution was restored to room temperature, and neutralized with saturated sodium bicarbonate water. This was extracted with ethyl acetate, and washed with saturated sodium bicarbonate water and saturated saline water. After dried, the solvent was evaporated away to obtain the entitled compound as a pale yellow solid.

Reference Example 2

6-(Methylsulfonyl)-3-pyridinol

Bis(pinacolate)diboron (6.6 g), potassium acetate (5.9 g) and (1,1'-bis(diphenylphosphino)ferrocene)dichloropalladium(II)/dichloromethane complex (980 mg) were added to a dimethylsulfoxide (80 ml) solution of 3-bromo-6-(methylsulfonyl)pyridine (4.72 g), and the reaction solution was stirred at 80° C. for 2 hours. Ethyl acetate and water were added to the reaction solution, the insoluble matter was removed by filtration through Celite, and the organic layer was separated. The organic layer was washed with water and saturated saline water, then dried over anhydrous magnesium sulfate, and the solvent was evaporated away under reduced pressure.

At 0° C., aqueous 5 N sodium hydroxide solution (60 ml) and 30% hydrogen peroxide water (30 ml) were added to a tetrahydrofuran (200 ml) solution of the obtained residue, then the reaction solution was stirred overnight at room temperature. The reaction solution was diluted with diethyl ether, then washed with water. The aqueous layer was made acidic with 5 N hydrochloric acid, and extracted with ethyl acetate. The organic layer was dried over anhydrous magnesium sulfate, and the solvent was evaporated away under reduced pressure. The obtained residue was washed with a chloroform/hexane mixed solvent to obtain the entitled compound as a brown solid.

Reference Example 3

6-(Ethylsulfonyl)-3-pyridinol

Using 3-chloro-6-(ethylsulfonyl)pyridine and in the same manner as in Reference Example 2, or according to a method similar to it, or according to a combination of the method with an ordinary method, the entitled compound was obtained.

Reference Example 4

6-(5-Methyl-1,2,4-oxadiazol-3-yl)-3-pyridinol (Step 1)

Synthesis of 6-bromo-3-pyridinol

With cooling with ice, isopropylmagnesium chloride (2 M tetrahydrofuran solution) (435 mg) was added to a tetrahydrofuran (800 ml) solution of 2,5-dibromopyridine (200 g), and stirred at room temperature for 1.5 hours. With cooling with ice, a tetrahydrofuran (200 ml) solution of triisopropyl borate (214 mg) was added, and stirred overnight at room temperature. With cooling with ice, the reaction solution was gradually added to a water (2.5 L) solution of sodium hydroxide (160 g). Water (1 L) and hexane (1 L) were added, and the aqueous layer was extracted. With cooling with ice, hydrogen peroxide water (30%) (150 ml) was gradually added to the aqueous layer, taking 1 hour, and then stirred overnight at room temperature. With cooling with ice, the reaction solution was neutralized with concentrated hydrochloric acid, then extracted with ethyl acetate, and the organic layer was washed with saturated saline water. After dried, the solvent was evaporated away under reduced pressure to obtain the entitled compound (130 g).

(Step 2)

Synthesis of 2-bromo-5-(methoxymethoxy)pyridine

Methoxymethyl chloride (73 ml) was added to a tetrahydrofuran (1.3 L) solution of the obtained 6-bromo-3-pyridinol (129 g), and sodium hydride (30% liquid paraffin added) (32 g) was added at an inner temperature not to be over −10° C. Water was added, extracted with ethyl acetate, and the organic layer was washed with saturated saline water. After dried, the solvent was evaporated away under reduced pressure, and the residue was purified by silica gel column chromatography (developing solvent: hexane/ethyl acetate=9/1 to 8/1) to obtain the entitled compound (105 g) as a colorless oil.

(Step 3)

Synthesis of 5-(methoxymethoxy)-2-pyridinecarbonitrile

Zinc cyanide (88.9 g) and tetrakis(triphenylphosphine)palladium(0) (29.1 g) were added to a dimethylformamide (1100 ml) solution of the obtained oil (105 g), and stirred under heat at 105° C. for 1 hour. After restored to room temperature, ethyl acetate (1.5 L) and water (1.2 L) were added, and extracted with ethyl acetate. The organic layer was washed with saturated saline water, dried, the solvent was evaporated away under reduced pressure, and the residue was purified by silica gel column chromatography (developing solvent: hexane/ethyl acetate=8/1 to 7/1 to 2/1) to obtain the entitled compound (53.4 g).

(Step 4)

Synthesis of
6-(5-methyl-1,2,4-oxadiazol-3-yl)-3-pyridinol

With cooling with ice, hydroxylamine (aqueous 50% solution) (35.4 ml) was added to an ethanol (400 ml) solution of the obtained product (41 g), and stirred at room temperature for 30 minutes. With cooling with ice, water (1 L) was added, and stirred for 1 hour. The formed crystal was collected by filtration to obtain a product (39.5 g).

Acetic acid (200 ml) was added to the obtained crystal (39.5 g), and with cooling with ice, acetic anhydride (20.8 ml) was added, and stirred at room temperature for 1 hour. This was kept heated at 70° C., and stirred overnight. The reaction solvent was evaporated away under reduced pressure, and trifluoroacetic acid (100 ml) was added to the obtained brown solid, and stirred at room temperature for 3 hours. The solvent was evaporated away under reduced pressure, a mixed solvent of hexane/ethyl acetate=20/1 was added, and stirred. The formed solid was collected by filtration, and dried to obtain the entitled compound (57.1 g) as its trifluoroacetate.

Reference Example 6

2-Ethynylpyrazine

This was synthesized according to the method described in Crystal Growth & Design, 2003, Vol. 3, No. 4, pp. 573-580.

INDUSTRIAL APPLICABILITY

The 2-heteroaryl-substituted indole derivative or its pharmaceutical salt of formula (I) of the invention has an excellent glucokinase activating effect, and is therefore useful in the field of medicine for remedy and/or prevention of diabetes, diabetes complications or obesity.

What is claimed is:
1. A compound represented by formula (I):

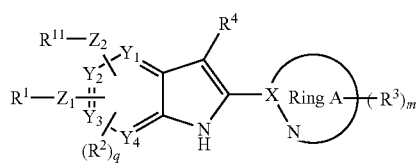

or a pharmaceutically acceptable salt thereof, wherein:
$R^1$ represents an aryl or a heteroaryl group having from 1 to 3 heteroatoms selected from the group consisting of a nitrogen atom, a sulfur atom and an oxygen atom;
$R^{11}$ represents an aryl, or a 5- to 7-membered aliphatic heterocyclic ring or a 5- or 6-membered heteroaryl group having from 1 to 3 heteroatoms selected from the group consisting of a nitrogen atom, a sulfur atom and an oxygen atom;
said $R^1$ and $R^{11}$ may be mono to tri-substituted with the same or different groups selected from $R^5$;

each $R^2$ independently represents formyl, —OH, —$C_{1-6}$ alkyl, —$CH_{3-a}F_a$, —$OCH_{3-a}F_a$, amino, cyano, halogen or —$(CH_2)_{1-4}$—OH; wherein a is an integer of 1 to 3;
each $R^3$ independently represents —$C_{1-6}$ alkyl, —$(CH_2)_{1-6}$—OH, —C(O)—O$C_{1-6}$ alkyl, —$(CH_2)_{1-6}$—O$C_{1-6}$ alkyl, —$(CH_2)_{1-6}$—$NH_2$, cyano, —C(O)—$C_{1-6}$ alkyl, halogen, —$C_{2-6}$ alkenyl, —O$C_{1-6}$ alkyl, —COOH or —OH;
$R^4$ represents a hydrogen atom or —$C_{1-6}$ alkyl;
each $R^5$ independently represents —$C_{1-6}$ alkyl optionally substituted with from 1 to 3 hydroxy, halogen, —OC(O)—$C_{1-6}$ alkyl optionally substituted with from 1 to 3 halogens, or —O$C_{1-6}$ alkyl groups;
—$C_{3-7}$ cycloalkyl;
—$C_{2-6}$ alkenyl;
—C(O)—N($R^{51}$)$R^{52}$;
—S(O)$_2$—N($R^{51}$)$R^{52}$;
—O—$C_{1-6}$ alkyl optionally substituted with halogen or N($R^{51}$)$R^{52}$;
—S(O)$_{0-2}$—$C_{1-6}$ alkyl;
—C(O)—$C_{1-6}$ alkyl optionally substituted with halogen, amino, CN, hydroxy, —O—$C_{1-6}$ alkyl, —$CH_{3-a}F_a$, —OC(O)—$C_{1-6}$ alkyl, —N($C_{1-6}$alkyl)C(O)O—$C_{1-6}$ alkyl, —NH—C(O)O—$C_{1-6}$ alkyl, phenyl, —N($R^{51}$)$R^{52}$, —NH—C(O)—$C_{1-6}$ alkyl, —N($C_{1-6}$ alkyl)-C(O)—$C_{1-6}$ alkyl or —NH—S(O)$_{0-2}$—$C_{1-6}$ alkyl:
—C(S)—$C_{3-7}$ cycloalkyl;
—C(S)—$C_{1-6}$ alkyl;
—C(O)—O—$C_{1-6}$ alkyl;
—$(CH_2)_{0-4}$—N($R^{53}$)—C(O)—$R^{54}$;
—N($R^{53}$)—C(O)—O—$R^{54}$;
—C(O)-aryl optionally substituted with halogen;
—C(O)-aromatic hetero ring;
—C(O)-aliphatic hetero ring;
a heterocyclic ring optionally substituted with unsubstituted —$C_{1-6}$ alkyl or —$C_{1-6}$ alkyl substituted with halogen or —O—$C_{1-6}$ alkyl;
a phenyl optionally substituted with halogen, —$C_{1-6}$ alkyl or —O—$C_{1-6}$ alkyl;
a halogen, CN, formyl, COOH, amino, oxo, hydroxy, hydroxyamidino or nitro;
$R^{51}$ and $R^{52}$ each independently represent a hydrogen atom or —$C_{1-6}$ alkyl, or $R^{51}$ and $R^{52}$, taken together, form a 4- to 7-membered heterocyclic ring;
$R^{53}$ represents a hydrogen atom or —$C_{1-6}$ alkyl;
$R^{54}$ represents —$C_{1-6}$ alkyl, or $R^{53}$ and $R^{54}$ and —N—C(O)—O—, taken together, form a 4- to 7-membered, nitrogen-containing aliphatic heterocyclic ring optionally substituted with oxo, or the aliphatic heterocyclic ring may have 1 or 2 double bonds in the ring;
$Z_1$ represents —O—;
$Z_2$ represents a single bond, —O—, or —$CH_2$— in which the —$CH_2$— may be substituted with halogen, $C_{1-6}$ alkyl, hydroxy, cyano or —O—$C_{1-6}$ alkyl,
$Y_1, Y_2, Y_3$ and $Y_4$ independently represent a carbon atom;
the ring A represents a heteroaryl group having, in the ring, from 1 to 4 hetero atoms selected from the group consisting of a nitrogen atom, a sulfur atom and an oxygen atom, and represented by a formula (II):

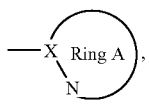

X represents a carbon atom,
m represents an integer of from 0 to 2; and
q represents an integer of from 0 to 2.

2. A compound according to claim 1 wherein the ring A is thiazolyl, imidazolyl, isothiazolyl, thiadiazolyl, oxadiazolyl, triazolyl, oxazolyl, isoxazolyl, pyrazinyl, pyridyl, pyridazinyl, pyrazolyl or pyrimidinyl optionally substituted with from 1 to 3 $R^5$ groups,
or a pharmaceutically acceptable salt thereof.

3. A compound according to claim 1, wherein $R^{11}$ is an aryl, or a pharmaceutically acceptable salt thereof.

4. A compound according to claim 1, wherein $R^{11}$ is a 5- to 7-membered aliphatic heterocyclic ring having, from 1 to 3 heteroatoms selected from the group consisting of a nitrogen atom, a sulfur atom and an oxygen atom, or a pharmaceutically acceptable salt thereof.

5. A compound according to claim 1 wherein $R^{11}$ is a 5- or 6-membered heteroaryl group having, from 1 to 3 heteroatoms selected from the group consisting of a nitrogen atom, a sulfur atom and an oxygen atom, or a pharmaceutically acceptable salt thereof.

6. A compound selected from the group consisting of:
7-(2-fluorophenoxy)-5-(4-(methylsulfonyl)phenoxy)-2-pyridin-2-yl-1H-indole,
7-(2-fluorophenoxy)-5-(4-(methylsulfonyl)phenoxy)-2-pyrazin-2-yl-1H-indole,
7-(2,6-difluorophenoxy)-5-(4-(methylsulfonyl)phenoxy)-2-pyrazin-2-yl-1H-indole,
7-(2,6-difluorophenoxy)-5-((6-(methylsulfonyl)pyridin-3-yl)oxy)-2-pyridin-2-yl-1H-indole,
7-(2,6-difluorophenoxy)-5-(4-(ethylsulfonyl)phenoxy)-2-pyrazin-2-yl-1H-indole,
7-(2,6-difluorophenoxy)-5-((6-(ethylsulfonyl)pyridin-3-yl)oxy)-2-pyridin-2-yl-1H-indole,
7-(2-cyanophenoxy)-5-((6-(ethylsulfonyl)pyridin-3-yl)oxy)-2-pyridin-2-yl-1H-indole,
2-((5-((6-(methylsulfonyl)pyridin-3-yl)oxy)-2-pyridin-2-yl-1H-indol-6-yl)oxy)-3-fluorobenzonitrile,
2-((5-((6-(ethylsulfonyl)pyridin-3-yl)oxy)-2-pyridin-2-yl-1H-indol-6-yl)oxy)-3-fluorobenzonitrile,
1-methyl-3-((5-(4-methylsulfonyl)phenoxy)-2-pyridin-2-yl-1H-indol-7-yl)oxy)pyridin-2(1H)-one,
1-methyl-3-((5-(4-ethylsulfonyl)phenoxy)-2-pyridin-2-yl-1H-indol-7-yl)oxy)pyridin-2(1H)-one,
5-((6-(ethylsulfonyl)pyridin-3-yl)oxy-7-(2-methoxyphenoxy)-2-pyridin-2-yl-1H-indole,
5-((6-(ethylsulfonyl)pyridin-3-yl)oxy-7-((2-methoxypyridin-3-yl)oxy)-2-pyridin-2-yl-1H-indole,
6-((2-(difluoromethoxy)pyridin-3-yl)oxy)-5-((6-(ethylsulfonyl)pyridin-3-yl)oxy)-2-pyridin-2-yl-1H-indole,
6-((2-(difluoromethoxy)pyridin-3-yl)oxy)-5-((6-(ethylsulfonyl)pyridin-3-yl)oxy-2-pyrazin-2-yl-1H-indole,
6-((2-(difluoromethoxy)pyridin-3-yl)oxy)-5-(4-(ethylsulfonyl)phenoxy)-2-pyridin-2-yl-1H-indole,
6-((2-(difluoromethoxy)pyridin-3-yl)oxy)-5-((6-(methylsulfonyl)pyridin-3-yl)oxy-2-pyridin-2-yl-1H-indole,
6-((2-chloropyridin-3-yl)oxy)-5-((6-(ethylsulfonyl)pyridin-3-yl)oxy-2-pyridin-2-yl-1H-indole,
3-((5-((6-(ethylsulfonyl)pyridin-3-yl)oxy)-2-pyridin-2-yl-1H-indol-6-yl)oxy)pyridin-2-carbonitrile,
6-(2,6-difluorophenoxy)-5-((6-(ethylsulfonyl)pyridin-3-yl)oxy)-2-pyrazin-2-yl-1H-indole,
6-(2,6-difluorophenoxy)-5-((6-(ethylsulfonyl)pyridin-3-yl)oxy)-2-pyridin-2-yl-1H-indole,
6-(2,6-difluorophenoxy)-5-((6-(ethylsulfonyl)pyridin-3-yl)oxy)-2-(1-methyl-1H-pyrazol-3-yl)-1H-indole,
6-(2,6-difluorophenoxy)-5-((6-(ethylsulfonyl)pyridin-3-yl)oxy)-2-(1H-pyrazol-3-yl)-1H-indole,
6-(2,6-difluorophenoxy)-5-((6-(ethylsulfonyl)pyridin-3-yl)oxy)-2-(1,2,4-thiadiazol-5-yl)-1H-indole,
6-(2,6-difluorophenoxy)-5((6-(ethylsulfonyl)pyridin-3-yl)oxy)-2-(1,3,4-thiadiazol-2-yl)-1H-indole,
2-((5-(4-(methylsulfonyl)phenoxy)-2-pyridin-2-yl-1H-indol-6-yl)oxy)benzamide,
4-((6-(2-aminocarbonyl)phenoxy)-2-pyridin-2-yl-1H-indol-5-yl)oxy)-N,N-dimethylbenzamide,
2-((5-((6-(ethylsulfonyl)pyridin-3-yl)oxy)-2-pyridin-2-yl-1H-indol-6-yl)oxy)benzonitrile,
2-((5-((6-(ethylsulfonyl)pyridin-3-yl)oxy)-2-pyrazin-2-yl-1H-indol-6-yl)oxy)benzonitrile,
5-((6-(ethylsulfonyl)pyridin-3-yl)oxy-6-((2-methoxypyridin-3-yl)oxy)-2-pyridin-2-yl-1H-indole,
5-((6-(ethylsulfonyl)pyridin-3-yl)oxy-6-(2-methoxyphenoxy)-2-pyridin-2-yl-1H-indole,
1-((5-((6-(methylsulfonyl)pyridin-3-yl)oxy)-2-pyridin-2-yl-1H-indol-6-yl)methyl)pyrrolidin-2-one,
1-((5-((6-(5-methyl-1,2,4-oxadiazol-3-yl)pyridin-3-yl)oxy)-2-pyridin-2-yl-1H-indol-6-yl)methyl)pyrrolidin-2-one,
1-((3-methyl-5-((6-(methylsulfonyl)pyridin-3-yl)oxy)-2-pyridin-2-yl-1H-indol-6-yl)methyl)pyrrolidin-2-one,
1-((5-((6-(methylsulfonyl)pyridin-3-yl)oxy)-2-pyrazin-2-yl-1H-indol-6-yl)methyl)pyrrolidin-2-one,
1-((5-((6-(ethylsulfonyl)pyridin-3-yl)oxy)-2-pyridin-2-yl-1H-indol-6-yl)methyl)pyrrolidin-2-one,
1-((5-(4-(ethylsulfonyl)phenoxy)-2-pyridin-2-yl-1H-indol-6-yl)methyl)pyrrolidin-2-one,
1-((5-(4-(5-methyl-1,2,4-oxadiazol-3-yl)phenoxy)-2-pyridin-2-yl-1H-indol-6-yl)methyl)pyrrolidin-2-one,
1-((5-((6-(methoxymethyl)pyridin-3-yl)oxy)-2-pyrazin-2-yl-1H-indol-6-yl)methyl)pyrrolidin-2-one,
1-((5-((6-(methoxymethyl)pyridin-3-yl)oxy)-2-pyridin-2-yl-1H-indol-6-yl)methyl)pyrrolidin-2-one,
5-(4-methylsulfonyl)phenoxy)-6-((1-methyl)-1H-tetrazol-5-yl)methyl)-2-pyridin-2-yl-1H-indole,
3-((5-((6-ethylsulfonyl)pyridin-3-yl)oxy)-2-pyridin-2-yl-1H-indol-6-yl)methyl)-1,3-oxazolidin-2-one,
3-((5-((6-ethylsulfonyl)pyridin-3-yl)oxy)-2-pyridin-2-yl-1H-indol-6-yl)methyl)-1,3-thiazolidin-2-one, and
6-(1-acetylpyrrolidin-2-yl)-5-((6-(ethylsulfonyl)pyridin-3-yl)oxy)-2-pyridin-2-yl-1H-indole, or a pharmaceutically acceptable salt thereof.

7. A pharmaceutical composition comprising a compound in accordance with claim 1 in combination with a pharmaceutically acceptable carrier.

8. A pharmaceutical composition comprised of a compound in accordance with claim 6, or a pharmaceutically acceptable salt thereof, in combination with a pharmaceutically acceptable carrier.

* * * * *